US006451568B1

(12) United States Patent
McMaster et al.

(10) Patent No.: US 6,451,568 B1
(45) Date of Patent: Sep. 17, 2002

(54) CLONING OF HUMAN CHOLINE ETHANOLAMINEPHOSPHO TRANSFERASES SYNTHESIS OF PHOSPHATIDYL CHOLINE PHOSPHATIDYLE THANOLAMINE AND PLATELET ACTIVATING FACTOR

(75) Inventors: Christopher McMaster; Anette Henneberry, both of Nova Scotia (CA)

(73) Assignee: Dalhousie University, Halifax ( * ) Notice: Subject to any disclaimer, the term of this patent is extended or adjusted under 35 U.S.C. 154(b) by 0 days.

(21) Appl. No.: 09/719,083

(22) PCT Filed: Jun. 7, 1999

(86) PCT No.: PCT/CA99/00513

§ 371 (c)(1),
(2), (4) Date: Dec. 8, 2000

(87) PCT Pub. No.: WO99/64605

PCT Pub. Date: Dec. 16, 1999

Related U.S. Application Data

(60) Provisional application No. 60/088,379, filed on Jun. 8, 1998.

(51) Int. Cl.[7] .............................. C12P 7/64; C12N 9/12; C12N 5/02; C07H 21/04
(52) U.S. Cl. ......................... 435/134; 435/41; 435/194; 435/325; 435/410; 435/252.3; 435/252.33; 435/254.11; 435/320.1; 536/23.1; 536/23.2; 536/23.5
(58) Field of Search ................................ 435/194, 324, 435/410, 254.11, 252.3, 252.33, 320.1, 41, 134; 536/23.2, 23.1, 23.5

(56) References Cited

PUBLICATIONS

Hennebery et al. "Cloning and expression of human chline/ ethanolaminephosphotransferase: . . . " Biochem. J. (1999) 339, 291–298.*

Hjelmstad and Bell, Mutants of *Saccharomyces cerevisiae* Defective in sn–1,2–Diacylglycerol Cholinephosphotransferase, 1987, JBC 262: 3909–3917.

Hjelmstad and Bell, The sn–1,2–Diacylglycerol Ethanolaminephosphotransferase Activity of *Saccharomyces cerevisiae*, 1988, JBC 263: 19748–19757.

Hjelmstad and Bell, sn–1,2–Diacylglycerol Choline– and Ethanolaminephosphotransferases in *Saccharomyces cerevisiae*, 1991, JBC 266: 5094–5103.

Hjelmstad and Bell, The sn–1,2–Diacylglycerol Cholinephosphotransferase of *Saccharomyces cerevisiae*, 1990, JBC 265: 1755–1764.

Hjelmstad and Bell, sn–1,2–Diacylglycerol Choline– and Ethanolaminephosphotransferases in *Saccharomyces cerevisiae*, 1991, JBC 266: 4357–4365.

McMaster and Bell, Phosphatidylcholine Biosynthesis in *Saccharomyces cerevisiae*, 1994, JBC 269: 28010–28016.

MaMaster et al, Phospholipid and cation activation of chimaeric cholie / ethanolamine phosphotransferases, 1996, *Biochem J* 313: 729–735.

Hjelmstad et al, Chimeric Enzymes, 1994, JBC 269: 20995–21002.

Williams and McMaster, Scanning Alanine Mutagenesis of the CDP–alcohol Phosphotransferase Motif of *Saccharomyces cerevisiae* Cholinephosphotransferase, 1998, JBC 273: 13482–13487.

Min et al, Cloning of an Aminoalcoholphosphotransferase cDNA from Chinese Cabbage Roots, 1997, *J Plant Bio* 40: 234–239.

Dewey et al, The AAPT1 gene of Soybean Complements a Cholinephosphotransferase–Deficient Mutant of Yeast, 1994, *The Plant Cell* 6: 1495–1507.

* cited by examiner

*Primary Examiner*—Nashaat T. Nashed
(74) *Attorney, Agent, or Firm*—Michael R. Williams; Adrian D. Battison; Ryan W. Dupuis

(57) ABSTRACT

We report the first cloning and expression, from a mammalian source, of proteins capable of catalyzing choline- and ethanolaminephosphotransferase reactions (hCEPT1 and hCEPT2). Both coding regions predict highly hydrophobic proteins of 43–46.5 kDa with several predicted membrane spanning domains. A CDP-alcohol phosphotransferase motif, DG(x)2AR(x)8G(x)3D(x)3D, has been identified in both hCEPT1 and hCEPT2 choline- and ethanolaminephosphotransferases (and several other lipid synthesizing enzymes that catalyze the formation of a phosphoester bond by the displacement of CMP from a CDP-alcohol by a second alcohol). Site-directed mutagenesis was used to differentiate the residues responsible for choline- versus ethanolamine-phosphotransferase activity. Mutation of glycine 156 of hCEPT1 abolished ethanolaminephosphotransferase activity, while cholinephosphotransferase activity remained intact.

9 Claims, 16 Drawing Sheets

| | | | | |
|---|---|---|---|---|
| GGCACGAGCT | GGAGTCGGAG | GCGATATTTC | TAGGGGTGTA | 40 |
| CTTGTTGGGG | TCAGGGTAAG | CACCAGCCAC | AAAAACCTAC | 80 |
| AAAAGAAGGG | AAATTACTGT | CTTTAAATAT | TAAAAAAAAA | 120 |
| CAAGATCCAT | GAGTGGGCAT | CGATCAACAA | GGAAAAGATG | 160 |
| TGGAGATTCT | CACCCGGAGT | CCCCAGTGGG | CTTCGGGCAT | 200 |
| ATGAGTACTA | CAGGATGTGT | ATTAAATAAA | TTGTTTCAGT | 240 |
| TACCAACACC | ACCATTGTCA | AGACACCAAC | TAAAGCGGCT | 280 |
| AGAAGAACAC | AGATATCAAA | GTGCTGGACG | GTCCCTGCTT | 320 |
| GAGCCCTTAA | TGCAAGGGTA | TTGGGAATGG | CTCGTTAGAA | 360 |
| GAGTTCCCTC | CTGGATTGCC | CCAAATCTCA | TCACCATCAT | 400 |
| TGGACTGTCA | ATAAACATCT | GTACAACTAT | TTTATTAGTC | 440 |
| TTCTACTGCC | CTACAGCTAC | AGAGCAGGCA | CCTCTGTGGG | 480 |
| CATATATTGC | TTGTGCCTGT | GGCCTTTTCA | TTTACCAGTC | 520 |
| TTTGGATGCT | ATTGATGGGA | AACAGGCAAG | AAGAACCAAT | 560 |
| AGTAGTTCTC | CTCTGGAGA | ACTTTTGAT | CATGGCTGTG | 600 |
| ATTCACTATC | AACAGTTTTT | GTGGTTCTTG | GAACTTGTAT | 640 |
| TGCAGTGCAG | CTGGGACAA | ACCCTGATTG | GATGTTTTT | 680 |
| TGTTGTTTTG | CGGGACATT | TATGTTCTAT | TGTGCGCACT | 720 |
| GGCAAACGTA | TGTTTCTGGA | ACATTGCGAT | TTGGAATAAT | 760 |
| TGATGTGACT | GAAGTGCAAA | TCTTCATAAT | AATCATGCAT | 800 |
| TTGCTGGCAG | TGATTGGAGG | ACCACCTTTT | TGGCAATCTA | 840 |
| TGATTCCAGT | GCTGAATATT | CAAATGAAAA | TTTTTCCTGC | 880 |
| ACTTTGTACT | GTAGCAGGGA | CCATATTTTC | CTGTACAAAT | 920 |
| TACTTCCGTG | TAATCTTCAC | AGGTGGTGTT | GGCAAAAATG | 960 |
| GATCAACAAT | AGCAGGAACA | AGTGTCCTTT | CTCCTTTTCT | 1000 |
| CCATATTGGA | TCAGTGATTA | CATTAGCTGC | AATGATCTAC | 1040 |
| AAGAAATCTG | CAGTTCAGCT | TTTTGAAAAG | CATCCCTGTC | 1080 |
| TTTATATACT | GACATTTGGT | TTTGTGTCTG | CTAAAATCAC | 1120 |
| TAATAAGCTT | GTGGTTGCAC | ACATGACGAA | AAGTGAAATG | 1160 |
| CATTTGCATG | ACACAGCATT | CATAGGTCCG | GCACTTTTGT | 1200 |
| TTCTGGACCA | GTATTTAAC | AGCTTTATTG | ATGAATATAT | 1240 |
| TGTACTTTGG | ATTGCCCTGG | TTTTCTCTTT | CTTTGATTTG | 1280 |
| ATCCGCTACT | GTGTCAGTGT | TTGCAATCAG | ATTGCGTCTC | 1320 |
| ACCTGCACAT | ACATGTCTTC | AGAATCAAGG | TCTCTACAGC | 1360 |
| TCATTCTAAT | CATCATTAAT | GATGTAATTG | GTATATAGGA | 1400 |
| ACATCATGTT | TTCTGCAGGA | AAGAAAGTAA | CATATTAAGG | 1440 |

FIGURE 1A-1  SEQ ID NO:1

| | | | | |
|---|---|---|---|---|
| AGAATGGGGG | TGGATAAGAA | CAAATATAAT | TTATAATAAT | 1480 |
| CAATGTTGTA | TAACTTTTAT | TCTTTATTAT | TGGTAACACG | 1520 |
| CCCTAACTAT | CCTGTGTGAG | AATGGGAATT | TCAAGTCCCA | 1560 |
| TCTTGTAAAT | TGTATATGTT | GTCATGCAGG | GTTTGGGCCA | 1600 |
| AGAAAGCATG | CAGAAAAAAA | TGCCATGTGA | TTGTAATTAT | 1640 |
| CCTGGATTCA | GAATAATACT | GTGATGGGGA | GCCAGATCCG | 1680 |
| CAGTGGTGGA | GAGTTCTAAT | GTTGACTGTT | TGCAGGCCAA | 1720 |
| AAGATGATTG | CTTTATAATT | TTAACAAATC | ATTGTCTTTT | 1760 |
| AGTAACATCC | TTGTTTAGTG | TCTTCTCAAG | CTTTCTTTAC | 1800 |
| TGAGGAATTC | AGCTTGTGAC | ACAGATACAT | CCCACTAGCT | 1840 |
| TGTGAGGTGG | AACTAGTAAT | AAAGACCTTG | AATTTGGATT | 1880 |
| GAAAAGTTTC | CTATCTTTAC | ATTGTTGAGG | AAGTCCTTTT | 1920 |
| TTTTTTTTTT | TTTAATTGCT | CAAGAAATGA | TTCTCTCACA | 1960 |
| GGCTTGGGAA | ATCCTGTTAG | CATGCAGAAT | AATGTGGTAA | 2000 |
| CTTTGTCAAT | TTCCCATTTT | ATTTTTTTAA | ATAAATATAT | 2040 |
| GATCTAAACG | G | | | 2051 |

FIGURE 1A-2 SEQ ID NO:1

| | | | | |
|---|---|---|---|---|
| ATCGTATTAC | CATGGTGATG | CGTTTTGGCA | GTACATCAAT | 40 |
| GGGCGTGGAT | AGCGGTTTGA | CTCACGGGGA | TTTCCAAAGT | 80 |
| CTCCACCCCA | TTGACGTCAA | TGGGAGTTTG | TTTTGGCACC | 120 |
| AAAATCAACG | GGACTTTCCA | AAATGTCGTA | ACAACTCCGC | 160 |
| CCCATTGACG | CAAATGGGCG | GTAGGCGTGT | ACGGTGGGAG | 200 |
| GTCTATATAA | GCAGAGCTCG | TTTAGTGAAC | CGTCAGATCG | 240 |
| CCTGGAGACG | CCATCCACGC | TGTTTTGACC | TCCATAGAAG | 280 |
| ACACCGGGAC | CGATCCAGCC | TCCGGACTCT | AGCCTAGGCT | 320 |
| TTTGCAAAAA | GCTATTTAGG | TGACACTATA | GAAGGTACGC | 360 |
| CTGCAGGTAC | CGGTCCGGAA | TTCCCGGGTC | GACCCACGCG | 400 |
| TCCGGGCAGC | CGGGCAGGCC | GGCCTGACCT | CGACCTCCGC | 440 |
| CGTGCGGGCC | CGACCGGTGA | GTCCAGCCCG | GCAGTCGCAG | 480 |
| GACCCGGCCG | CCAGCCTCTC | CCTCCACCTC | TCCTGCCCC | 520 |
| CAGCGCCAGG | CGCGGGCTGC | GCTCGGTGGC | GGCGGCGGGG | 560 |
| CCCTCAGGCG | GCCATGGCGG | CAGGCGCCGG | GGCCGGGTCC | 600 |
| GCGCCGCGCT | GGCTGAGGGC | GCTGAGCGAG | CCGCTGAGCG | 640 |
| CGGCGCAGCT | GCGGCGACTG | GAGGAGCACC | GCTACAGCGC | 680 |
| GGCGGGCGTC | TCGCTGCTCG | AGCCGCCGCT | GCAGCTCTAC | 720 |
| TGGACCTGGC | TGCTCCAGTG | GATCCCGCTC | TGGATGGCCC | 760 |
| CCAACTCCAT | CACCCTGTTG | GGGCTCGCCG | TCAACGTGGT | 800 |
| CACCACGCTC | GTGCTCATCT | CCTACTGTCC | CACGGCCACC | 840 |
| GAAGAGGCAC | CATACTGGAC | ATACCTTTTA | TGTGCACTGG | 880 |
| GACTTTTTAT | TTACCAGTCA | CTGGATGCTA | TTGATGGGAA | 920 |
| ACAAGCCAGA | AGAACAAACT | CTTGTTCCCC | TTTAGGGGAG | 960 |
| CTCTTTGACC | ATGGCTGTGA | CTCTCTTTCC | ACAGTATTTA | 1000 |
| TGGCAGTGGG | AGCTTCAATT | GCCGCTCGCT | TAGGAACTTA | 1040 |
| TCCTGACTGG | TTTTTTTCCT | GCTCTTTTAT | TGGGATGTTT | 1080 |
| GTGTTTTATT | GCGCTCATTG | GCAGACTTAT | GTTTCAGGCA | 1120 |
| TGTTGAGATT | TGGAAAGTG | GATGTAACTG | AAATTCAGAT | 1160 |
| AGCTTTAGTG | ATTGTCTTTG | TGTTGTCTGC | ATTTGGAGGA | 1200 |
| GCAACAATGT | GGGACTATAC | GATTCCTATT | CTAGAAATAA | 1240 |
| AATTGAAGAT | CCTTCCAGTT | CTTGGATTTC | TAGGTGGAGT | 1280 |
| AATATTTTCC | TGTTCAAATT | ATTTCCATGT | TATCCTCCAT | 1320 |
| GGTGGTGTTG | GCAAGAATGG | ATCCACTATA | GCAGGCACCA | 1360 |
| GTGTCTTGTC | ACCTGGACTC | CACATAGGAC | TAATTATTAT | 1400 |
| ACTGGCAATA | ATGATCTATA | AAAAGTCAGC | AACTGATGTG | 1440 |
| TTTGAAAAGC | ATCCTTGTCT | TTATATCCTA | ATGTTTGGAT | 1480 |

FIGURE 1B-1 SEQ ID NO:3

```
GTGTCTTTGC  TAAAGTCTCA  CAAAAATTAG  TGGTAGCTCA  1520
CATGACCAAA  AGTGAACTAT  ATCTTCAAGA  CACTGTCTTT  1560
TTGGGGCCAG  GTCTTTTGTT  TTTAGACCAG  TACTTTAATA  1600
ATTTTATAGA  CGAATATGTT  GTTCTATGGA  TGGCAATGGT  1640
GATTTCTTCA  TTTGATATGG  TGATATACTT  TAGTGCTTTG  1680
TGCCTGCAAA  TTTCAAGACA  CCTTCATCTA  AATATATTCA  1720
AGACTGCATG  TCATCAAGCA  CCTGAACAGG  TTCAAGTTCT  1760
TTCTTCAAAG  AGTCATCAGA  ATAACATGGA  TTGAAGAGAC  1800
TTCCGAACAC  TTGCTATCTC  TTGCTGCTGC  TGTTTCATGG  1840
AAGGAGATAT  TAAACATTTG  TTTAATTTTT  ATTTAAGTGT  1880
TATACCTATT  TCAGCAAATA  AAATATTTCA  TTGCTTAAAA  1920
AAAAAAAAAA  AAAAAAAA                            1949
```

FIGURE 1B-2 SEQ ID NO:3

```
Met Ser Gly His Arg Ser Thr Arg Lys Arg   10
Cys Gly Asp Ser His Pro Glu Ser Pro Val   20
Gly Phe Gly His Met Ser Thr Thr Gly Cys   30
Val Leu Asn Lys Leu Phe Gln Leu Pro Thr   40
Pro Pro Leu Ser Arg His Gln Leu Lys Arg   50
Leu Glu Glu His Arg Tyr Gln Ser Ala Gly   60
Arg Ser Leu Leu Glu Pro Leu Met Gln Gly   70
Tyr Trp Glu Trp Leu Val Arg Arg Val Pro   80
Ser Trp Ile Ala Pro Asn Leu Ile Thr Ile   90
Ile Gly Leu Ser Ile Asn Ile Cys Thr Thr  100
Ile Leu Leu Val Phe Tyr Cys Pro Thr Ala  110
Thr Glu Gln Ala Pro Leu Trp Ala Tyr Ile  120
Ala Cys Ala Cys Gly Leu Phe Ile Tyr Gln  130
Ser Leu Asp Ala Ile Asp Gly Lys Gln Ala  140
Arg Arg Thr Asn Ser Ser Ser Pro Leu Gly  150
Glu Leu Phe Asp His Gly Cys Asp Ser Leu  160
Ser Thr Val Phe Val Val Leu Gly Thr Cys  170
Ile Ala Val Gln Leu Gly Thr Asn Pro Asp  180
Trp Met Phe Phe Cys Cys Phe Ala Gly Thr  190
Phe Met Phe Tyr Cys Ala His Trp Gln Thr  200
Tyr Val Ser Gly Thr Leu Arg Phe Gly Ile  210
Ile Asp Val Thr Glu Val Gln Ile Phe Ile  220
Ile Ile Met His Leu Leu Ala Val Ile Gly  230
Gly Pro Pro Phe Trp Gln Ser Met Ile Pro  240
Val Leu Asn Ile Gln Met Lys Ile Phe Pro  250
Ala Leu Cys Thr Val Ala Gly Thr Ile Phe  260
Ser Cys Thr Asn Tyr Phe Arg Val Ile Phe  270
Thr Gly Gly Val Gly Lys Asn Gly Ser Thr  280
Ile Ala Gly Thr Ser Val Leu Ser Pro Phe  290
Leu His Ile Gly Ser Val Ile Thr Leu Ala  300
```

FIGURE 2A-1  SEQ ID NO:2

```
Ala Met Ile Tyr Lys Lys Ser Ala Val Gln   310
Leu Phe Glu Lys His Pro Cys Leu Tyr Ile   320
Leu Thr Phe Gly Phe Val Ser Ala Lys Ile   330
Thr Asn Lys Leu Val Val Ala His Met Thr   340
Lys Ser Glu Met His Leu His Asp Thr Ala   350
Phe Ile Gly Pro Ala Leu Leu Phe Leu Asp   360
Gln Tyr Phe Asn Ser Phe Ile Asp Glu Tyr   370
Ile Val Leu Trp Ile Ala Leu Val Phe Ser   380
Phe Phe Asp Leu Ile Arg Tyr Cys Val Ser   390
Val Cys Asn Gln Ile Ala Ser His Leu His   400
Ile His Val Phe Arg Ile Lys Val Ser Thr   410
Ala His Ser Asn His His                   416
```

FIGURE 2A-2  SEQ ID NO:2

```
Met ala ala gly ala gly ala gly ser ala    10
pro arg trp leu arg ala leu ser glu pro    20
leu ser ala ala gln leu arg arg leu glu    30
glu his arg tyr ser ala ala gly val ser    40
leu leu glu pro pro leu gln leu tyr trp    50
thr trp leu leu gln trp ile pro leu trp    60
met ala pro asn ser ile thr leu leu gly    70
leu ala val asn val val thr thr leu val    80
leu ile ser tyr cys pro thr ala thr glu    90
glu ala pro tyr trp thr tyr leu leu cys   100
ala leu gly leu phe ile tyr gln ser leu   110
asp ala ile asp gly lys gln ala arg arg   120
thr asn ser cys ser pro leu gly glu leu   130
phe asp his gly cys asp ser leu ser thr   140
val phe met ala val gly ala ser ile ala   150
ala arg leu gly thr tyr pro asp trp phe   160
phe ser cys ser phe ile gly met phe val   170
phe tyr cys ala his trp gln thr tyr val   180
ser gly met leu arg phe gly lys val asp   190
val thr glu ile gln ile ala leu val ile   200
val phe val leu ser ala phe gly gly ala   210
thr met trp asp tyr thr ile pro ile leu   220
glu ile lys leu lys ile leu pro val leu   230
gly phe leu gly gly val ile phe ser cys   240
ser asn tyr phe his val ile leu his gly   250
gly val gly lys asn gly ser thr ile ala   260
gly thr ser val leu ser pro gly leu his   270
ile gly leu ile ile ile leu ala ile met   280
ile tyr lys lys ser ala thr asp val phe   290
glu lys his pro cys leu tyr ile leu met   300
phe gly cys val phe ala lys val ser gln   310
```

FIGURE 2B-1 SEQ ID NO:4

```
lys leu val val ala his met thr lys ser  320
glu leu tyr leu gln asp thr val phe leu  330
gly pro gly leu leu phe leu asp gln tyr  340
phe asn asn phe ile asp glu tyr val val  350
leu trp met ala met val ile ser ser phe  360
asp met val ile tyr phe ser ala leu cys  370
leu gln ile ser arg his leu his leu asn  380
ile phe lys thr ala cys his gln ala pro  390
glu gln val gln val leu ser ser lys ser  400
his gln asn asn met asp                   406
```

FIGURE 2B-2  SEQ ID NO:4

Northern blot analysis of hCEPT2 transcripts.

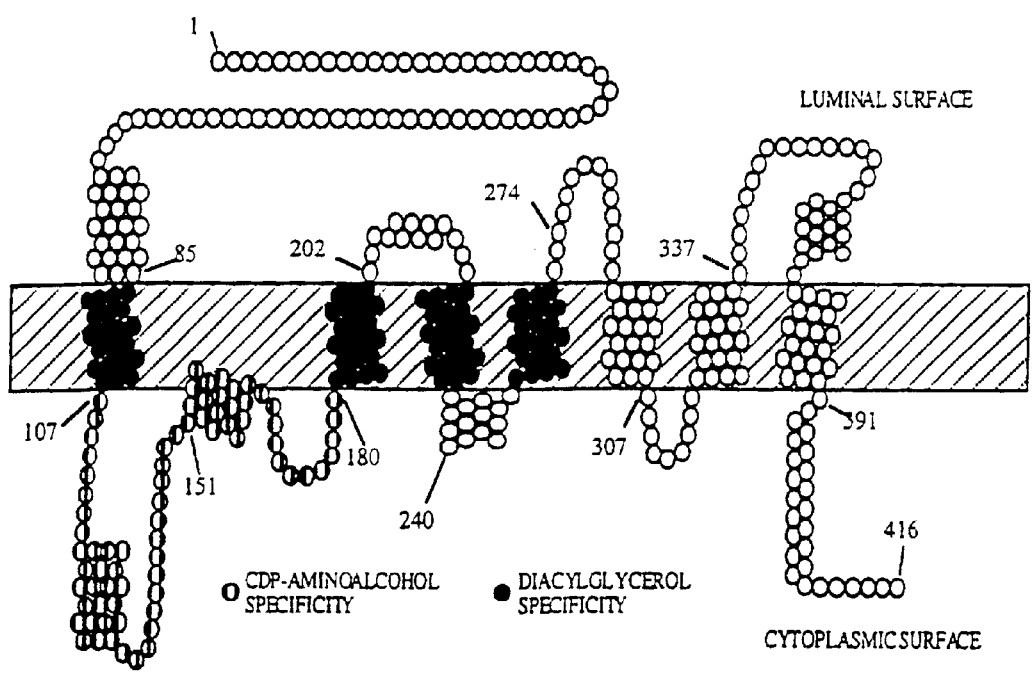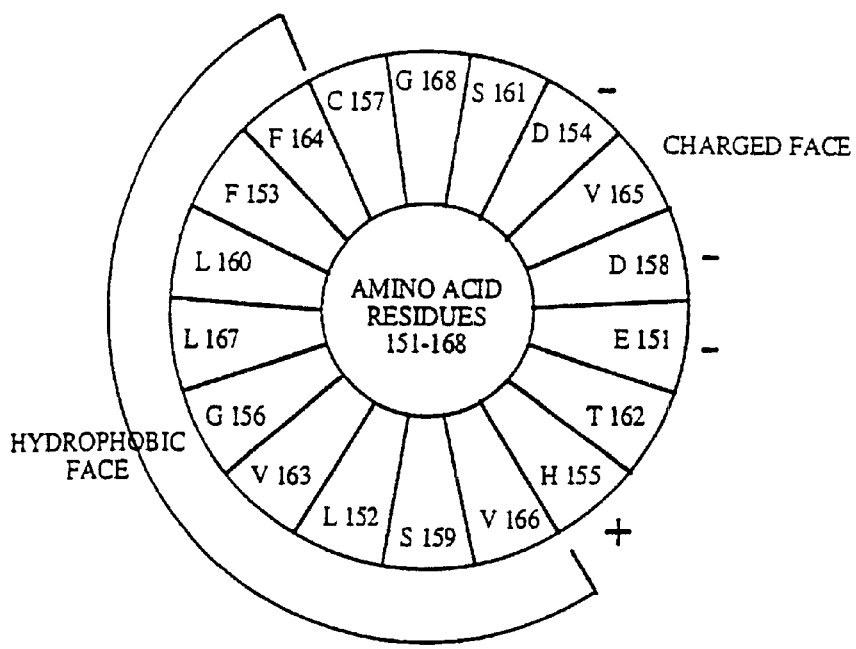
FIG. 6

FIG. 8
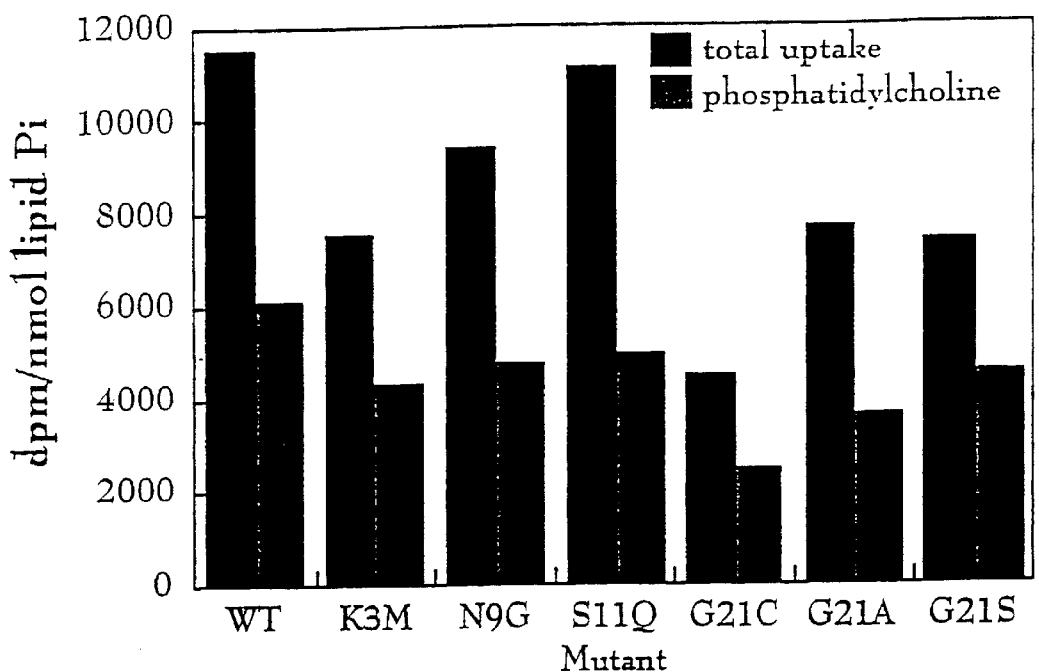
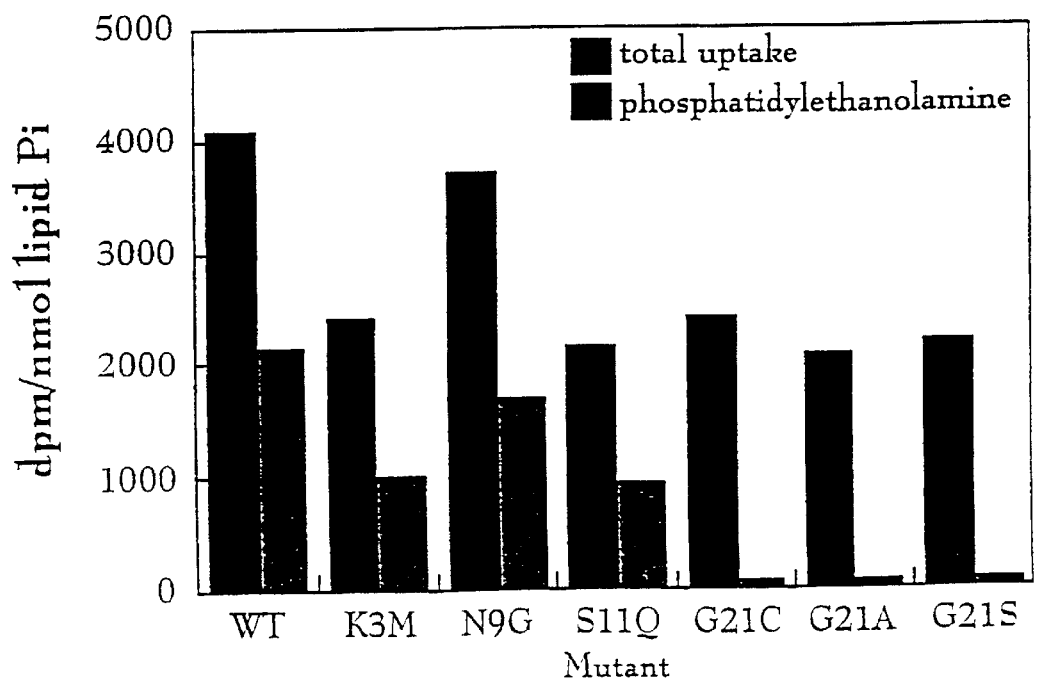

SEQUENCE LISTING

<160> NUMBER OF SEQ ID NOS: 12

<210> SEQ ID NO 1
<211> LENGTH: 2051
<212> TYPE: DNA
<213> ORGANISM: human Jurkat T cell cDNA library
<220> FEATURE:
<221> NAME/KEY: transit_peptide
<222> LOCATION: (129)..(1379)
<223> OTHER INFORMATION: Open reading frame encoding hCEP1 peptide

<400> SEQUENCE: 1

```
ggcacgagct ggagtcggag gcgatatttc tagggtgta cttgttgggg tcagggtaag      60
caccagccac aaaaacctac aaaagaaggg aaattactgt ctttaaatat taaaaaaaaa    120
caagatccat gagtgggcat cgatcaacaa ggaaaagatg tggagattct cacccggagt    180
ccccagtggg cttcggcat atgagtacta caggatgtgt attaaataaa ttgtttcagt     240
taccaacacc accattgtca agacaccaac taaagcggct agaagaacac agatatcaaa    300
gtgctggacg gtccctgctt gagcccttaa tgcaaggta ttgggaatgg ctcgttagaa     360
gagttccctc ctggattgcc ccaaatctca tcaccatcat ggactgtca ataaacatct     420
gtacaactat tttattagtc ttctactgcc ctacagctac agagcaggca cctctgtggg    480
catatattgc ttgtgcctgt ggccttttca tttaccagtc tttggatgct attgatggga    540
aacaggcaag aagaaccaat agtagttctc ctctgggaga acttttgat catggctgtg     600
attcactatc aacagttttt gtggttcttg gaacttgtat tgcagtgcag ctggggacaa    660
accctgattg gatgtttttt tgttgttttg cggggacatt tatgttctat tgtgcgcact    720
ggcaaacgta tgtttctgga acattgcgat ttggaataat tgatgtgact gaagtgcaaa    780
tcttcataat aatcatgcat ttgctggcag tgattggagg accacctttt tggcaatcta    840
tgattccagt gctgaatatt caaatgaaaa ttttcctgc actttgtact gtagcaggga    900
ccatattttc ctgtacaaat tacttccgtg taatcttcac aggtggtgtt ggcaaaaatg    960
gatcaacaat agcaggaaca agtgtccttt ctccttttct ccatattgga tcagtgatta   1020
cattagctgc aatgatctac aagaaatctg cagttcagct ttttgaaaag catccctgtc   1080
tttatatact gacatttggt tttgtgtctg ctaaaatcac taataagctt gtggttgcac   1140
acatgacgaa aagtgaaatg catttgcatg acacagcatt cataggtccg gcacttttgt   1200
ttctggacca gtattttaac agctttattg atgaatatat tgtactttgg attgccctgg   1260
ttttctcttt ctttgatttg atccgctact gtgtcagtgt ttgcaatcag attgcgtctc   1320
acctgcacat acatgtcttc agaatcaagg tctctacagc tcattctaat catcattaat   1380
gatgtaattg gtatatagga acatcatgtt ttctgcagga aagaaagtaa catattaagg   1440
agaatggggg tggataagaa caaatataat ttataataat caatgttgta taacttttat   1500
tctttattat tggtaacacg ccctaactat cctgtgtgag aatgggaatt tcaagtccca   1560
tcttgtaaat tgtatatgtt gtcatgcagg gtttgggcca agaaagcatg cagaaaaaaa   1620
tgccatgtga ttgtaattat cctggattca gaataatact gtgatgggga gccagatccg   1680
cagtggtgga gagttctaat gttgactgtt tgcaggccaa aagatgattg ctttataatt   1740
ttaacaaatc attgtctttt agtaacatcc ttgtttagtg tcttctcaag cttttctttac   1800
tgaggaattc agcttgtgac acagatacat cccactagct tgtgaggtgg aactagtaat   1860
aaagaccttg aatttggatt gaaaagtttc ctatctttac attgttgagg aagtccttt    1920
```

-continued

```
tttttttttt tttaattgct caagaaatga ttctctcaca ggcttgggaa atcctgttag    1980
catgcagaat aatgtggtaa ctttgtcaat ttcccatttt atttttttaa ataaatatat    2040
gatctaaacg g                                                        2051
```

<210> SEQ ID NO 2
<211> LENGTH: 416
<212> TYPE: PRT
<213> ORGANISM: human Jurkat T cell cDNA library

<400> SEQUENCE: 2

```
Met Ser Gly His Arg Ser Thr Arg Lys Arg Cys Gly Arg Ser His Pro
 1               5                  10                  15

Glu Ser Pro Val Gly Phe Gly His Met Ser Thr Thr Gly Cys Val Leu
            20                  25                  30

Asn Lys Leu Phe Gln Leu Pro Thr Pro Pro Leu Ser Arg His Gln Leu
        35                  40                  45

Lys Arg Leu Glu Glu His Arg Tyr Gln Ser Ala Gly Arg Ser Leu Leu
    50                  55                  60

Glu Pro Leu Met Gln Gly Tyr Trp Glu Trp Leu Val Arg Arg Val Pro
65                  70                  75                  80

Ser Trp Ile Ala Pro Asn Leu Ile Thr Ile Gly Leu Ser Ile Asn
                85                  90                  95

Ile Cys Thr Thr Ile Leu Leu Val Phe Tyr Cys Pro Thr Ala Thr Glu
            100                 105                 110

Gln Ala Pro Leu Trp Ala Tyr Ile Ala Cys Ala Cys Gly Leu Phe Ile
        115                 120                 125

Tyr Gln Ser Leu Asp Ala Ile Asp Gly Lys Gln Ala Arg Arg Thr Asn
    130                 135                 140

Ser Ser Ser Pro Leu Gly Glu Leu Phe Asp His Gly Cys Asp Ser Leu
145                 150                 155                 160

Ser Thr Val Phe Val Val Leu Gly Thr Cys Ile Ala Val Gln Leu Gly
                165                 170                 175

Thr Asn Pro Asp Trp Met Phe Phe Cys Cys Phe Ala Gly Thr Phe Met
            180                 185                 190

Phe Tyr Cys Ala His Trp Gln Thr Tyr Val Ser Gly Thr Leu Arg Phe
        195                 200                 205

Gly Ile Ile Asp Val Thr Glu Val Gln Ile Phe Ile Ile Met His Leu
    210                 215                 220

Leu Ala Val Ile Gly Gly Pro Pro Phe Trp Gln Ser Met Ile Pro
225                 230                 235                 240

Val Leu Asn Ile Gln Met Lys Ile Phe Pro Ala Leu Cys Thr Val Ala
                245                 250                 255

Gly Thr Ile Phe Ser Cys Thr Asn Tyr Phe Arg Val Ile Phe Thr Gly
            260                 265                 270

Gly Val Gly Lys Asn Gly Ser Thr Ile Ala Gly Thr Ser Val Leu Ser
        275                 280                 285

Pro Phe Leu His Ile Gly Ser Val Ile Thr Leu Ala Ala Met Ile Tyr
    290                 295                 300

Lys Lys Ser Ala Val Gln Leu Phe Glu Lys His Pro Cys Leu Tyr Ile
305                 310                 315                 320

Leu Thr Phe Gly Phe Val Ser Ala Lys Ile Thr Asn Lys Leu Val Val
                325                 330                 335

Ala His Met Thr Lys Ser Glu Met His Leu His Asp Thr Ala Phe Ile
```

|     |     |     |     |     |     |     |     |     |     |     |     |
| --- | --- | --- | --- | --- | --- | --- | --- | --- | --- | --- | --- |
|     |     | 340 |     |     | 345 |     |     | 350 |     |     |     |
| Gly | Pro | Ala | Leu | Leu | Phe | Leu | Asp | Gln | Tyr | Phe | Asn | Ser | Phe | Ile | Asp |
|     |     |     |     | 355 |     |     |     |     | 360 |     |     |     | 365 |     |     |
| Glu | Tyr | Ile | Val | Leu | Trp | Ile | Ala | Leu | Val | Phe | Ser | Phe | Phe | Asp | Leu |
|     | 370 |     |     |     |     | 375 |     |     |     |     | 380 |     |     |     |     |
| Ile | Arg | Tyr | Cys | Val | Ser | Val | Cys | Asn | Gln | Ile | Ala | Ser | His | Leu | His |
| 385 |     |     |     |     | 390 |     |     |     |     | 395 |     |     |     |     | 400 |
| Ile | His | Val | Phe | Arg | Ile | Lys | Val | Ser | Thr | Ala | His | Ser | Asn | His | His |
|     |     |     |     | 405 |     |     |     |     | 410 |     |     |     | 415 |     |     |

<210> SEQ ID NO 3
<211> LENGTH: 1939
<212> TYPE: DNA
<213> ORGANISM: human placenta cDNA library
<220> FEATURE:
<221> NAME/KEY: transit_peptide
<222> LOCATION: (574)..(1794)
<223> OTHER INFORMATION: Open reading frame encoding hCEP2 peptide

<400> SEQUENCE: 3

| | | |
|---|---|---|
| atcgtattac catggtgatg cgttttggca gtacatcaat gggcgtggat agcggtttga | 60 |
| ctcacgggga tttccaaagt ctccacccca ttgacgtcaa tgggagtttg ttttggcacc | 120 |
| aaaatcaacg ggactttcca aaatgtcgta acaactccgc cccattgacg caaatgggcg | 180 |
| gtaggcgtgt acggtgggag gtctatataa gcagagctcg tttagtgaac cgtcagatcg | 240 |
| cctggagacg ccatccacgc tgttttgacc tccatagaag acaccgggac cgatccagcc | 300 |
| tccggactct agcctaggct tttgcaaaaa gctatttagg tgacactata gaaggtacgc | 360 |
| ctgcaggtac cggtccggaa ttcccgggtc gacccacgcg tccgggcagc cgggcaggcc | 420 |
| ggcctgacct cgacctccgc cgtgcgggcc cgaccggtga gtccagcccg gcagtcgcag | 480 |
| gacccggccg ccagcctctc cctccacctc tccctgcccc cagcgccagg cgcgggctgc | 540 |
| gctcggtggc ggcggcgggg ccctcaggcg gccatggcgg caggcgccgg ggccgggtcc | 600 |
| gcgccgcgct ggctgagggc gctgagcgag ccgctgagcg cggcgcagct gcggcgactg | 660 |
| gaggagcacc gctacagcgc ggcgggcgtc tcgctgctcg agccgccgct gcagctctac | 720 |
| tggacctggc tgctccagtg gatcccgctc tggatgcccc caactccat cacctgttg | 780 |
| gggctcgccg tcaacgtggt caccacgctc gtgctcatct cctactgtcc cacggccacc | 840 |
| gaagaggcac catactggac ataccttta tgtgcactgg actttttat ttaccagtca | 900 |
| ctggatgcta ttgatgggaa acaagccaga agaacaaact cttgttcccc tttaggggat | 960 |
| ctctttgacc atggctgtga ctctctttcc acagtattta tggcagtggg agcttcaatt | 1020 |
| gccgctcgct taggaactta tcctgactgg tttttttcct gctcttttat tgggatgttt | 1080 |
| gtgttttatt gcgctcattg gcagacttat gtttcaggca tgttgagatt tggaaaagtg | 1140 |
| gatgtaactg aaattcagat agctttagtg attgtctttg tgttgtctgc atttggagga | 1200 |
| gcaacaatgt gggactatac gattcctatt ctagaaataa aattgaagat ccttccagtt | 1260 |
| cttggatttc taggtggagt aatattttcc tgttcaaatt atttccatgt tatcctccat | 1320 |
| ggtggtgttg gcaagaatgg atccactata gcaggcacca gtgtcttgtc acctggactc | 1380 |
| cacataggac taattattat actggcaata atgatctata aaaagtcagc aactgatgtg | 1440 |
| tttgaaaagc atccttgtct ttatatccta atgtttggat gtgtcttgc taaagtctca | 1500 |
| caaaaattag tggtagctca catgaccaaa agtgaactat atcttcaaga cactgtcttt | 1560 |
| ttggggccag gtctttttgtt tttagaccag tactttaata attttataga cgaatatgtt | 1620 |

-continued

```
gttctatgga tggcaatggt gatttcttca tttgatatgg tgatatactt tagtgctttg     1680
tgcctgcaaa tttcaagaca ccttcatcta aatatattca agactgcatg tcatcaagca     1740
cctgaacagg ttcaagttct ttcttcaaag agtcatcaga ataacatgga ttgaagagac     1800
ttccgaacac ttgctatctc ttgctgctgc tgtttcatgg aaggagatat taaacatttg     1860
tttaattttt atttaagtgt tatacctatt tcagcaaata aatatttca ttgcttaaaa      1920 aaaaaaaaaa aaaaaaaaa                                                  1939
```

<210> SEQ ID NO 4
<211> LENGTH: 406
<212> TYPE: PRT
<213> ORGANISM: human placenta cDNA library

<400> SEQUENCE: 4

```
Met Ala Gly Ala Gly Ala Gly Ser Ala Pro Arg Trp Leu Arg Ala
 1               5                  10                  15

Leu Ser Glu Pro Leu Ser Ala Ala Gln Leu Arg Arg Leu Glu Glu His
                20                  25                  30

Arg Tyr Ser Ala Ala Gly Val Ser Leu Leu Glu Pro Leu Gln Leu
            35                  40                  45

Tyr Trp Thr Trp Leu Leu Gln Trp Ile Pro Leu Trp Met Ala Pro Asn
         50                  55                  60

Ser Ile Thr Leu Leu Gly Leu Ala Val Asn Val Val Thr Thr Leu Val
 65                  70                  75                  80

Leu Ile Ser Tyr Cys Pro Thr Ala Thr Glu Glu Ala Pro Tyr Trp Thr
                85                  90                  95

Tyr Leu Leu Cys Ala Leu Gly Leu Phe Ile Tyr Gln Ser Leu Asp Ala
            100                 105                 110

Ile Asp Gly Lys Gln Ala Arg Arg Thr Asn Ser Cys Ser Pro Leu Gly
        115                 120                 125

Glu Leu Phe Asp His Gly Cys Asp Ser Leu Ser Thr Val Phe Met Ala
    130                 135                 140

Val Gly Ala Ser Ile Ala Ala Arg Leu Gly Thr Tyr Pro Asp Trp Phe
145                 150                 155                 160

Phe Ser Cys Ser Phe Ile Gly Met Phe Val Phe Tyr Cys Ala His Trp
                165                 170                 175

Gln Thr Tyr Val Ser Gly Met Leu Arg Phe Gly Lys Val Asp Val Thr
            180                 185                 190

Glu Ile Gln Ile Ala Leu Val Ile Val Phe Val Leu Ser Ala Phe Gly
        195                 200                 205

Gly Ala Thr Met Trp Asp Tyr Thr Ile Pro Ile Leu Glu Ile Lys Leu
    210                 215                 220

Lys Ile Leu Pro Val Leu Gly Phe Leu Gly Val Ile Phe Ser Cys
225                 230                 235                 240

Ser Asn Tyr Phe His Val Ile Leu His Gly Gly Val Gly Lys Asn Gly
                245                 250                 255

Ser Thr Ile Ala Gly Thr Ser Val Leu Ser Pro Gly Leu His Ile Gly
            260                 265                 270

Leu Ile Ile Ile Leu Ala Ile Met Ile Tyr Lys Lys Ser Ala Thr Asp
        275                 280                 285

Val Phe Glu Lys His Pro Cys Leu Tyr Ile Leu Met Phe Gly Cys Val
    290                 295                 300

Phe Ala Lys Val Ser Gln Lys Leu Val Val Ala His Met Thr Lys Ser
```

```
305                 310                 315                 320
Glu Leu Tyr Leu Gln Asp Thr Val Phe Leu Gly Pro Gly Leu Leu Phe
                325                 330                 335

Leu Asp Gln Tyr Phe Asn Asn Phe Ile Asp Glu Tyr Val Val Leu Trp
            340                 345                 350

Met Ala Met Val Ile Ser Ser Phe Asp Met Val Ile Tyr Phe Ser Ala
        355                 360                 365

Leu Cys Leu Gln Ile Ser Arg His Leu His Leu Asn Ile Phe Lys Thr
    370                 375                 380

Ala Cys His Gln Ala Pro Glu Gln Val Gln Val Leu Ser Ser Lys Ser
385                 390                 395                 400

His Gln Asn Asn Met Asp
                405

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: EST 67440
      specific primer

<400> SEQUENCE: 5
gtctgccaat gagcgcaata a                                              21

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: nested EST
      67440 specific primer

<400> SEQUENCE: 6
ccagtcagga taagttccta agcga                                          25

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: EST 67440
      5' primer

<400> SEQUENCE: 7
ggcacgagta ccagtcac                                                  18

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: exterior
      primer for cDNA cloning

<400> SEQUENCE: 8
cagtaggaga tgagcacgag cgtg                                           24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: nested
```

-continued

```
      primer for cDNA cloning

<400> SEQUENCE: 9
gtgaccacgt tgacggcgag cccc                                            24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: probe used
      for colony screening

<400> SEQUENCE: 10
ctgctccagt ggatcccgct ctgg                                            24

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: cDNA
      cloning primer

<400> SEQUENCE: 11
tatcggcggg tggagcaccg ctacagc                                         27

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: CDP alcohol
      phosphotransferase motif
<220> FEATURE:
<221> NAME/KEY: NON_CONS
<222> LOCATION: (3)..(4)
<220> FEATURE:
<221> NAME/KEY: NON_CONS
<222> LOCATION: (7)..(14)
<220> FEATURE:
<221> NAME/KEY: NON_CONS
<222> LOCATION: (16)..(18)
<220> FEATURE:
<221> NAME/KEY: NON_CONS
<222> LOCATION: (20)..(22)

<400> SEQUENCE: 12

Asp Gly Xaa Xaa Ala Arg Xaa Xaa Xaa Xaa Xaa Xaa Xaa Gly Xaa
  1               5                  10                  15

Xaa Xaa Asp Xaa Xaa Xaa Asp
            20
```

CLONING OF HUMAN CHOLINE ETHANOLAMINEPHOSPHO TRANSFERASES SYNTHESIS OF PHOSPHATIDYL CHOLINE PHOSPHATIDYLE THANOLAMINE AND PLATELET ACTIVATING FACTOR

This application claims the benefit of provisional application No. 60/088,379 filed Jun. 8, 1998.

The present invention relates generally to the field of lipid biochemistry. More specifically, the present invention relates to the cloning of human choline/ethanolaminephosphotransferases.

BACKGROUND OF THE INVENTION

Cholinephosphotransferase catalyzes the final step in the synthesis of PtdCho through the Kennedy (CDP-choline) pathway via the transfer of a phosphocholine moiety from CDP-choline to diacylglycerol with the release of CMP and the formation of PtdCho (Vance, 1996 in *Biochemistry of Lipids, Lipoproteins and Membranes*, Vance, D E and Vance, J E, Elsevier: Amsterdam, pp 153–182; Kennedy and Weiss, 1956, *J Biol Chem* 222:193–214; Weiss et al, 1958, *J Biol Chem* 231:53–64; McMaster and Bell, 1997, *Biochim Biophys Acta* 1348:100–110; Hjelmstad and Bell, 1991, *J Biol Chem* 266:4357–4365; McMaster and Bell, 1994, *J Biol Chem* 269:28010–28016; and Cornell, 1989 in *Phosphatidylcholine Metabolism*, Vance, D E, Boca Raton: Fla., pp. 47–64). The fatty acyl composition of the diacylglycerol molecule utilized by cholinephosphotransferase determines the fatty acyl array for de novo synthesized PtdCho. In addition, the intracellular location of cholinephosphotransferase identifies the site of de novo PtdCho synthesis for subsequent transfer to other organelles, or assembly with proteins and other lipids for secretion during the synthesis of lung surfactant, lipoproteins, and bile (Jobe, 1993, *N Engl J Med* 328:861–868; Steinberg, 1997, *J Biol Chem* 272 2Q963–20966; Ruetz and Gros, 1994, *Cell* 77:1071–1081).

Properties of cholinephosphotransferase activities present in membrane preparations have identified an activity capable of de novo synthesis of the PtdCho structural analogues, platelet activating factor (PAF), a major mediator of inflammatory processes, as well as PAF precursor (Snyder, 1997, *Biochim Biophys Acta* 1348:111–116; Leslie, 1997, *J Biol Chem* 272:16709–16712; Venable et al, 1993, *J Lipid Res* 34:691–702). However, the biological and biochemical roles of a de novo synthesized PAF pathway, and indeed the roles of the various proposed isoforms of cholinephosphotransferase in the regulation of the partitioning of lipid biosynthetic pathways, have yet to be determined as a mammalian cholinephosphotransferase has not been cloned or purified.

Genetic approaches led to the isolation of two genes encoding cholinephosphotransferase activities from the yeast *Saccharomyces cerevisiae*. The yeast CPT1 gene product encodes a cholinephosphotransferase (McMaster and Bell, 1994; Hjelmstad and Beg, 1990, *J Biol Chem* 265:1755–1764: Hjelmstad and Bell, 1987, *J Biol Chem* 262:3909–3917) specific for the synthesis of PtdCho in vitro and in vivo, while the EPT1 gene product codes for a dual specificity choline/ethanolaminephosphotransferase capable of synthesizing PtdCho and phosphatidylethanolamine (PtdEtn) in vitro, but which synthesizes primarily PtdEtn in vivo (McMaster and Bell, 1994; Hjelmstad and Bell, 1991, *J Biol Chem* 266:5094–5103). Analysis of chimeric CPT1/EPT1 enzymes (McMaster and Bell, 1994; Hjelmstad and Bell, 1991; Hjelmstad and Bell, 1988. *J Biol Chem* 263:19748–19757) mapped the active site domain, and site-directed mutagenesis identified a diagnostic catalytic motif (Hjelmstad et al, 1994, *J Biol Chem* 269:2009521002). It was hypothesized that active site residues would be conserved between Genera. This rationale was used as a basis to isolate human choline/ethanolaminephosphotransferase cDNAs (hCEPT1 and hCEPT2) for subsequent expression and characterization.

SUMMARY OF THE INVENTION

According to a first aspect of the invention, there is provided an isolated native, cloned, recombinant or synthetic DNA sequence encoding hCEPT1 protein comprising nucleotides 497–2051 of SEQ ID NO,: or sub-fragments thereof.

According to a second aspect of the invention, there is provided an hCEPT1 protein having an amino acid sequence substantially as shown in SEQ ID NO:2.

According to a third aspect of the invention, there is provided a DNA molecule encoding hCEPT1 protein, said DNA deduced from the amino acid sequence of SEQ ID NO2.

According to a fourth aspect of the invention, there is provided an isolated native, cloned, recombinant or synthetic DNA sequence encoding hCEPT2 protein comprising nucleotides 1–881 of SEQ ID NO:3 or sub-fragments thereof.

According to a fifth aspect of the invention, there is provided hCEPT2 protein having an amino acid sequence substantially as shown in SEQ ID NO:4.

According to a sixth aspect of the invention, there is provided a DNA molecule encoding hCEPT1 protein, said DNA deduced from the amino acid sequence according to SEQ ID NO:4.

According to a seventh aspect of the invention, there is provided a recombinant expression system, capable, when transformed into a host cell, of expressing a DNA sequence encoding hCEPT1 (SEQ ID NO:2) or hCEPT2 (SEQ ID NO:3) which system comprises control sequences effective in said host cell operably linked to said DNA sequence.

According to an eighth aspect of the invention, there is provided a host cell transformed with the expression system described above.

The host cell may be selected from the group consisting of: a plant cell; a yeast cell; a bacterial cell; and a mammalian cell.

According to a ninth aspect of the invention, there is provided mutant hCEPT1 protein having an amino acid sequence substantially as shown in FIG. 2A (SEQ ID NO:2) and having a missense mutation at glycine 156.

According to a tenth aspect of the invention, there is provided a DNA molecule encoding mutant hCEPT1 protein, said DNA deduced from the amino acid sequence described above.

According to an eleventh aspect of the invention, there is provided mutant hCEPT2 protein having an amino acid sequence substantially as shown in FIG. 2B (SEQ ID NO:4) and having a missense mutation at glycine 156.

According to a twelfth aspect of the invention, there is provided a DNA molecule encoding mutant hCEPT2 protein, said DNA deduced from the amino acid sequence described above.

According to a thirteenth aspect of the invention, there are provided antibodies directed against hCEPT, said hCEPT selected from the group consisting of: hCEPT1 (SEQ ID NO:2); hCEPT2 (SEQ ID NO:4); mutant hCEPT1 protein having an amino acid sequence substantially as shown in SEQ ID NO:2 and having a missense mutation at glycine 156; mutant hCEPT2 protein having an amino acid sequence substantially as shown in SEQ ID NO:4 and having a missense mutation at glycine 156; and immunoreactive fragments thereof.

The antibodies described above may be used to identify proteins related to hCEPT1 and hCEPT2 or for diagnostic use.

According to a fourteenth aspect of the invention, there is provided a method of synthesizing lipids containing a given fatty acid composition comprising:

providing hCEPT protein, selected from the group consisting of: hCEPT1 (SEQ ID NO:2); hCEPT2 (SEQ ID NO:4); mutant hCEPT1 protein having an amino acid sequence substantially as shown in SEQ ID NO:2 and having a missense mutation at glycine 156; mutant hCEPT2 protein having an amino acid sequence substantially as shown in SEQ ID NO:4 and having a missense mutation at glycine 156; and combinations thereof;

providing substrates required for lipid biosynthesis;

combining the hCEPT protein and the substrates;

incubating the hCEPT protein and the substrates under conditions promoting lipid biosynthesis; and harvesting the lipids.

According to a fifteenth aspect of the invention, there is provided lipids prepared according to the above-described method.

The lipids may be used as a food additive.

According to a sixteenth aspect of the invention, there is provided a method of assaying a compound for modulation of lipid metabolism comprising:

providing hCEPT protein, selected from the group consisting of: hCEPT1 (SEQ ID NO:2); hCEPT2 (SEQ ID NO:4); mutant hCEPT1 protein having an amino acid sequence substantially as shown in SEQ ID NO:2 and having a missense mutation at glycine 156; mutant hCEPT2 protein having an amino acid sequence substantially as shown in SEQ ID NO:4 and having a missense mutation at glycine 156; and combinations thereof;

providing substrates required for lipid biosynthesis;

providing a compound proposed to modulate lipid metabolism;

combining the compound, the hCEPT protein and the substrates;

incubating the compound, the hCEPT protein and the substrates under conditions promoting lipid biosynthesis.

harvesting the lipids;

and characterizing the lipids, thereby determining the effect of the compound on lipid metabolism.

According to a seventeenth aspect of the invention, there is provided a reagent for use in disease diagnosis or genotyping comprising antibodies directed against hCEPT, said hCEPT selected from the group consisting of: hCEPT1 (SEQ ID NO:2); hCEPT2 (SEQ ID NO:4); mutant hCEPT1 protein having an amino acid sequence substantially as shown in SEQ ID NO:2 and having a missense mutation at glycine 156; mutant hCEPT2 protein having an amino acid sequence substantially as shown in SEQ ID NO:4 and having a missense mutation at glycine 156; and immunoreactive fragments thereof.

According to an eighteenth aspect of the invention, there is provided a reagent for use in identifying proteins related to hCEPT comprising antibodies directed against hCEPT, said hCEPT selected from the group consisting of: hCEPT1 (SEQ ID NO:2); hCEPT2 (SEQ ID NO: 4); mutant hCEPT1 protein having an amino acid sequence substantially as shown in SEQ ID NO:2 and having a missense mutation at glycine 156; mutant hCEPT2 protein having an amino acid sequence substantially as shown in SEQ ID NO:4 and having a missense mutation at glycine 156; and immunoreactive fragments thereof.

According to a nineteenth aspect of the invention, there is provided a nucleotide probe selected from the group consisting of: nucleotides 497–2051 of SEQ ID NO:1; nucleotides 1–881 of SEQ ID NO:3; and fragments thereof.

According to a twentieth aspect of the invention, there is provided an oligonucleotide for use in identifying genes related to hCEPT, said oligonucleotide selected from the group consisting of: nucleotides 497–2051 of SEQ ID NO:1; nucleotides 1–881 of SEQ ID NO:3; and fragments thereof.

According to a twenty-first aspect of the invention, there is provided an antisense probe for use in treating lipid metabolic disorders, said antisense probe being complementary to nucleotides 497–2051 of SEQ ID NO:1; nucleotides 1–881of SEQ ID NO:3; or fragments thereof.

One embodiment of the invention will now be described in conjunction with the accompanying figures in which:

BRIEF DESCRIPTION OF THE DRAWINGS

FIG. 1A is the nucleotide sequence of the isolated cDNA molecule hCEPT1 (SEQ ID NO:1); FIG. 1 B is the nucleotide sequence of the isolated cDNA molecule hCEPT2 (SEQ ID NO:3).

FIG. 2A is the amino acid sequence of hCEPT1 (SEQ ID NO:2); FIG. 2B is the amino acid sequence of hCEPT2 (SEQ ID NO:4).

FIGS. 6A and 6B show predicted secondary structures of hCEPT1 protein.

FIGS. 8A and 8B are bar graphs of metabolic labelling in hCEPT1 mutants.

Figure 3:
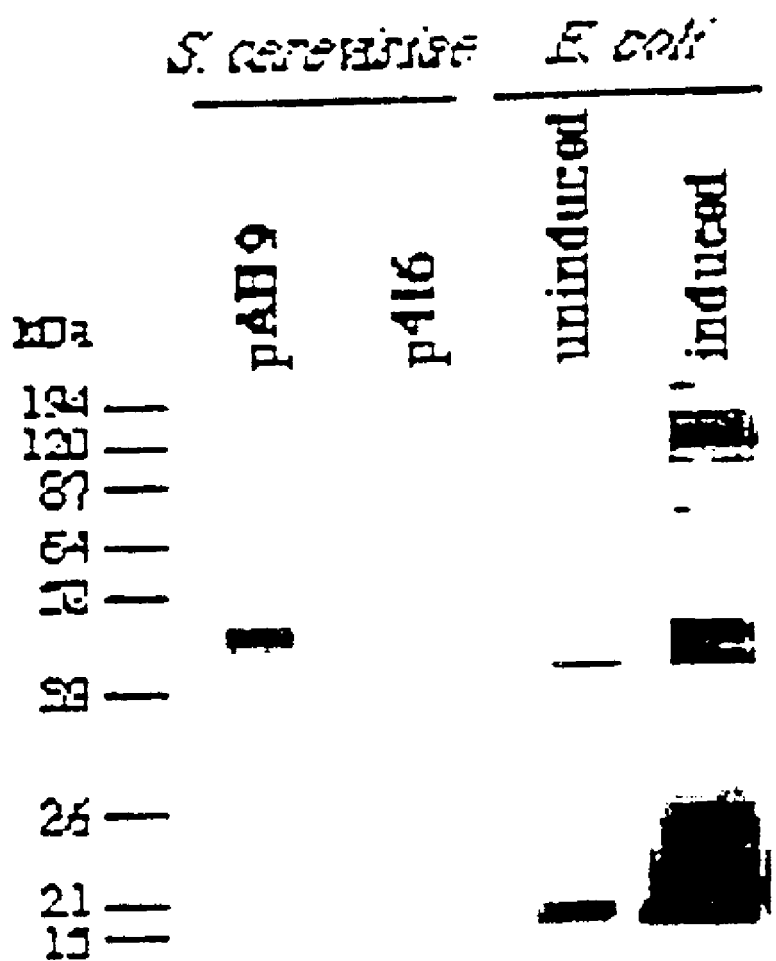
FIG. 3 is a Western Blot of hCEPT1 protein expressed in *S. cerevisiae* and *E. coli*.

Table 1 summarizes the diradylglycerol and CDP-aminoalcohol specificities of hCEPT1 protein.

Table 2 summarizes the results of overexpression of hCEPT1 and hCEPT2 in human HEK-293s cells.

DETAILED DESCRIPTION

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is the first cloning and expression from a mammalian source of proteins capable of catalyzing choline- and ethanolaminephosphotransferase reactions (hCEPT1 and hCEPT2). A CDP-alcohol phosphotransferase motif has been identified in both hCEPT1 and hCEPT2 and site-directed mutagenesis was subsequently used to determine the residue responsible for choline- versus ethanolamine-phosphotransferase activity. Specifically, mutation of glycine 156 of hCEPT1 abolished ethanolaminephosphotransferase activity without abolishing cholinephosphotransferase activity. Furthermore, this residue is conserved in hCEPT2.

hCEPT1 and hCEPT2 can be used for transferring phosphocholine or phosphoethanolamine to an acceptor lipid. These may include, but are in no way limited to, diacylglycerols, alkylacylglycerols and alkylalkylglycerols. Thus, the above-described enzymes may be used to synthesize lipids in vivo and in vitro. Furthermore, hCEPT1 and hCEPT2 can be used in assay systems for assessing the effect of different compounds on membrane composition which would in turn allow for the rapid identification of compounds capable of modulating lipid content. Given that the products of hCEPT1 and hCEPT2 include platelet activating factor, which is a mediator of inflammation and phosphatidylcholine, which is a component of lung surfactant, lipoproteins and bile, it is clear that compounds effective in treating a number of disorders could be identified in this way. Similarly, hCEPT1 and hCEPT2 could be used as gene therapy targets or antisense targets or as enzyme therapy agents for treating these disorders. Furthermore, hCEPT1 and hCEPT2 can be used to identify related enzymes. That is, nucleotide probes may be used to identify other isoforms of hCEPT1 and/or hCEPT2 and antibodies directed against the peptides or fragments thereof may be used to identify related enzymes in other organisms.

The invention will now be described by way of examples, although the invention is in no way limited to the examples.

EXAMPLE I

MATERIALS

[α-$^{32}$P]dATP (3000 Ci/mmol) and [γ-$^{32}$P]ATP (3000 Ci/mmol) were purchased from DuPont/NEN. [Methyl-$^{14}$C] CDP-choline and [methyl-$^{14}$C]choline were purchased from American Radiolabeled Chemicals. [Ethanolamine-1,2-$^{14}$C] CDP-ethanolamine and [1,2-$^{14}$C]ethanolamine were products of ICN. λGT11 forward sequencing primer, λGT11 human Quick-Clone™ cDNA libraries, and Advantage™ cDNA polymerase were purchased from Clontech. The pCMV-Sport human brain cDNA library, custom oligonucleotides, and T4 DNA ligase were products of Life Technologies. Manual dideoxy sequencing was performed utilizing the T7 sequencing kit (Pharmacia). Lipids were purchased from Avanti Polar Lipids. All other reagents were of the highest quality commercially available.

EXAMPLE II

ISOLATION AND EXPRESSION OF A FULL LENGTH CHOLINEPHOSPHOTRANSFERASE cDNA.

A tblastn search (McMaster et al, 1996, *Biochem J* 313:729–735) was performed versus the Expressed Sequence Tag (EST) data base using default parameters versus the predicted amino acid sequences of both the entire *S. cerevisiae* Cpt1p coding region and the Cpt1p CDP-alcohol phosphotransferase motif (Hjelmstad et al, 1994). An EST (human Jurkat T cell, Genbank accession number AA312638) was identified and sequenced in its entirety on both strands. A proposed coding region within the EST was amplified by PCR and subcloned into the Bam HI/Sal I sites of the *E. coli* expression vector pET23a (Novagen) resulting in the addition of an 11 amino acid T7 epitope tag (Williams and McMaster, 1998, *J Biol Chem* 273:13482–13487) to the N-terminus of the protein (pAH5). The T7 tagged version of hCEPT1 was excised from pAH5 with Bgl II and Sal I and subcloned into the constitutive *S. cerevisiae* expression vector p416 GPD (Gish and States, 1993, *Nature Genet* 3:266–272) creating pAH9. All PCR derived products were sequenced in their entirety.

EXAMPLE III

ISOLATION OF A FULL LENGTH hCEPT2 cDNA

The 365 bases of sequence deposited for the 1.1 kb EST clone 67440 (isolated from a Stratagene human placenta cDNA library) was initially identified based on significant homology to the active site of S. cerevisiae cholinephosphotransferase. EST clone 67440 was obtained from the IMAGE consortium and sequenced in its entirety on both strands utilizing a combination of manual dideoxy (Sambrook, J, Fritsch, E F, and Maniatis, T., 1989 in *Molecular Cloning: A Laboratory Manual*, Cold Spring Harbor Press, New York) and automated techniques (Li-cor apparatus, National Research Council of Canada/Dalhousie University joint laboratory). Comparison of the completed sequence of the EST 67440 cDNA to the known yeast (Hjelmstad and Bell, 1990 *J. Biol. Chem.* 265: 1755–1764; Hjelmstad and Bell, 1991, *J. Biol. Chem.* 266: 5094–5103), plant (Dewey et al, 1994, *Plant Cell* 6: 1495–1507), and our recently cloned human choline/ ethanolaminephosphotransferase 1 sequence described above revealed that the EST was incomplete at the 5' end. The 5' end was extended through two successive rapid amplification of cDNA ends (RACE) protocols (Innis, M. A. et al, 1990 in *PCR Protocols: A Guide to Methods and Applications*, Academic Press, Inc., San Diego) from human λGT11 cDNA libraries. First, a human placenta cDNA library (Clontech) was amplified utilizing λGT 11 forward primer and EST 67440 specific primers using a nested PCR approach. The first PCR reaction contained 20 mM Tris-HCl (pH 8.4), 50 mM KCl, 3 mM MgCl2, 0.2 mM dNTPs, 0.8 μM λGT11 forward primer, 0.8 μM EST 67440 specific primer GTCTGCCAATGAGCGCAATAA (SEQ ID NO: 5), 4 μl λGT11 human placenta cDNA library, 2.5 units Taq DNA polymerase (Life Technologies). PCR reaction conditions were performed for 30 cycles of 94° C. for 1 min, 55° C. for 1 min, and 72° C. for 2 min. A 5 μl aliquot was removed from this PCR reaction and used as template for a second PCR reaction performed under identical conditions as the above reaction except a nested EST 67440 specific primer CCAGTCAGGATAAGTTCCTAAGCGA (SEQ ID NO: 6) was utilized. A 3 μl aliquot of this second PCR reaction was TA cloned into pCR2.1 (Invitrogen) and transformed into *E. coli*. Transformants were selected on LB plates containing 100 μg/ml ampicillin. To identify inserts containing EST 67440 5' sequences, a 150 base pair probe was generated by PCR amplification of EST 67440 utilizing the primers CCAGTCAGGATAAGTTCCTAAGCGA (SEQ ID NO:6), and GGCACGAGTACCAGTCAC (SEQ ID NO:7). This EST 67440 specific probe was subjected to random prime labeling (Amersham Multiprime™ DNA labelling system). E. coli colonies containing TA cloned inserts were transferred to Hybond-N™ nylon membranes (Amersham) and screened by colony hybridization (Sambrook, J, Fritsch, E F, and Maniatis, T., 1989 in *Molecular Cloning: A Laboratory Manual*, Cold Spring Harbor Press, New York utilizing the labeled EST 67440 specific probe. Plasmids were prepared from positive colonies and inserts were sequenced. This strategy extended the sequence 164 bases towards the 5' end of the cDNA, however, after several attempts a complete cDNA was never recovered using the above primer set. To further extend the sequence, a universal human λGT11 cDNA library (Clontech) was subjected to the identical RACE strategy using primers derived from the extended sequence. The sequence of the exterior primer was CAGTAGGAGAT-GAGCACGAGCGTG (SEQ ID NO: 8) and the nested primer was GTGACCACGTTGACGGCGAGCCCC (SEQ ID NO:9). Colonies were screened using the oligo CTGCTCCAGTGGATCCCGCTCTGG (SEQ ID NO:10) end labelled with T4 kinase (Sambrook, J, Fritsch, E F, and Maniatis, T., 1989 in *Molecular Cloning: A Laboratory Manual*, Cold Spring Harbor Press, New York). The cDNA sequence was extended a further 158 bases using this strategy, however, the cDNA was still incomplete.

A full length cDNA was isolated using the Genetrapper™ system technology (Life Technologies). A primer corresponding to the most 5' RACE extneded sequence in hand, TATCGGCGGGTGGAGCACCGCTACAGC (SEQ ID NO: 11) was biotinylated using terminal deoxynucleotide transferase and hybridized in solution to a single stranded human brain cDNA library that had been generated by digestion of the library with Gene II protein and exonuclease III. Avidin bound to magnetic beads was used to selectively precipitate the biotinylated probe/hybridized cDNA complex, thus enriching the library for cDNAs complementary to the oligonucleotide used. The single stranded cDNAs were extended using Klenow and E. coli were transformed and screened for positive clones with the end labeled antisense oligo, CCAGTCAGGATAAGTTCCTAAGCGA, found within the original EST 67440. Plasmid DNA from positive colonies was amplified and hCEPT2 specific inserts confirmed and sized by PCR. The library was constructed in a vector for over-expression of the encoded cDNA in cell culture, hence, one of the positive hCEPT2 plasmids was selected for transfection of HEK293s cells (human placental kidney cell line) for subsequent enzyme assay analysis to confirm function.

EXAMPLE IV

NORTHERN BLOT

Figure 4A:
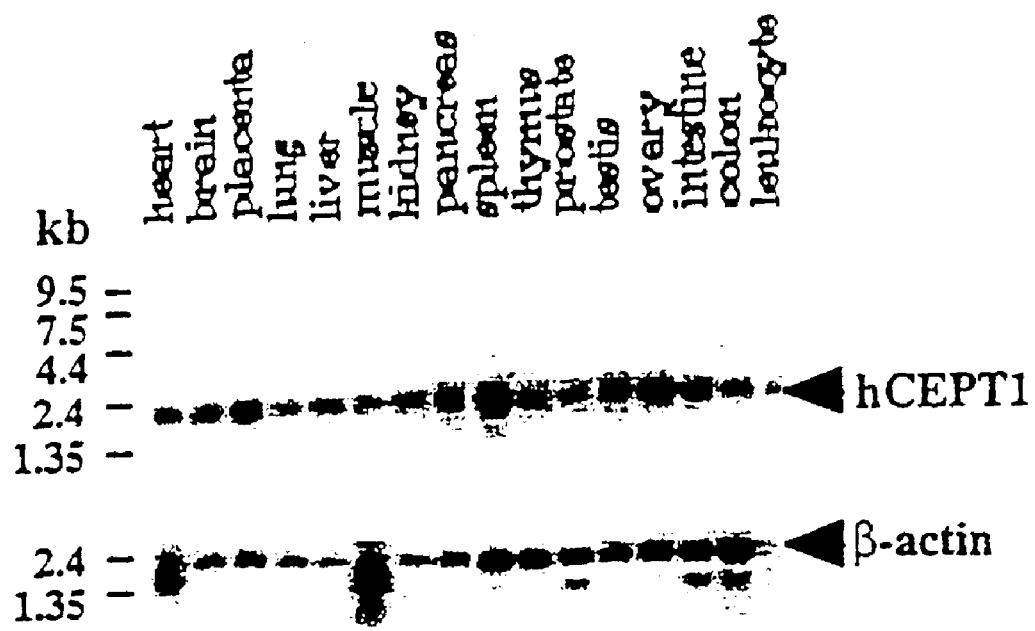
FIG. 4A is a Northern blot analysis of hCEPT1 and β-actin transcripts in human cell types.
Figure 4B:
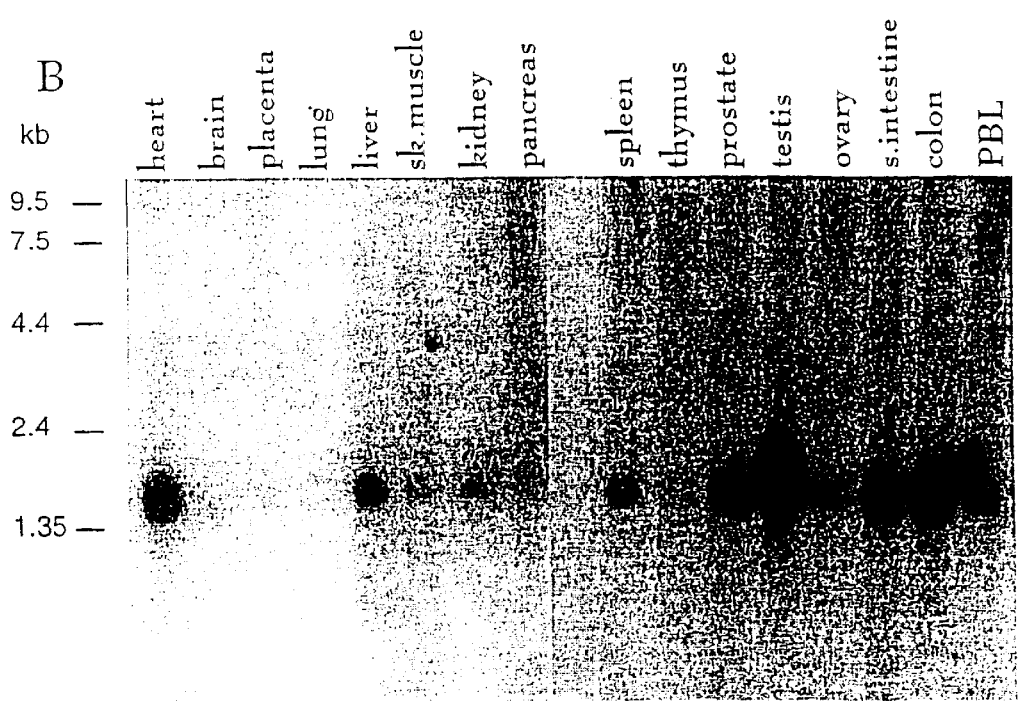
FIG. 4B is a Northern blot analysis of hCEPT2 transcripts in human cell types.

Random primed [$^{32}$P] labeled probes (Roberts and Green, 1994, *Nature* 371: 717–720) were synthesized versus either the entire 1.2 kb coding region of hCEPT1, the entire 1.2 kb coding region of hCEPT2 or a 2.0 kb region of human β-actin cDNA. Multiple human tissue Northern blots (Clontech) were hybridized at 68° C. in ExpressHyb™ solution (Munberg et al, 1995, *Gene* 156:119–122) for 1 hr and washed as per manufacturer's instructions. Blots were exposed to X-ray film for 1–3 days, as shown in FIG. 4.

EXAMPLE V

WESTERN BLOT

Microsomal membranes were prepared from BL21(DE3) pLysS *E. coil* and HJ091 *S. cerevisiae* cells (Hjelmstad et al, 1994) grown to mid-log phase in appropriate media to ensure plasmid maintenance (Feinberg and Vogeistein, 1984, *Anal Biochem* 137:266–267). Specifically, membrane preparations from *S. cerevisiae* strain HJ091 (cpt1::LEU2 ept1-) containing pAH9 or p416 GPD, or from *E. coli* BL21(DE3) pLysS containing pAH5 (± induction of protein with 0.4 mM IPTG for 2 hours at 25° C.) were separated by SDS-PAGE and blotted with a monoclonal antibody to the T7 epitope. Blots were probed with a T7 epitope tag specific monoclonal Ab (1:5,000, Novagen) coupled to horse radish peroxidase for detection using the ECL™ (Amersham) system, as shown in FIG. 3.

Alternatively, membranes were prepared from HJ091 *S. cerevisiae* cells (cpt1::LEU2 ept1-) (Williams and McMaster, 1998, *J. Biol. Chem* 273: 13482–13487) grown to mid-log phase in appropriate media to ensure plasmid maintenance (Kaiser, C., Michaelis, S., and Mitchell, A., 1994 in *Methods in Yeast Genetics*, Cold Spring Harbor Press, New York). The HJ091 strain of *S. cerevisiae* is devoid of endogenous choline- or ethanolamine-phosphotransferase activity due to inactivated alleles at the loci encoding for these activities (cpt1::LEU2 ept1-). Proteins were transferred to PVDF membranes (Harlow, E. and Lane, D., 1988 in *Antibodies: A Laboratory Manual*, Cold Spring Harbor Laboratory Press, New York) and blots were probed with a T7 epitope tag specific monoclonal Ab (1:5,000, Novagen) coupled to horse radish peroxidase for subsequent detection using the ECL™ (Amersham) system.

EXAMPLE VI

SITE-DIRECTED MUTAGENESIS

Figure 7:
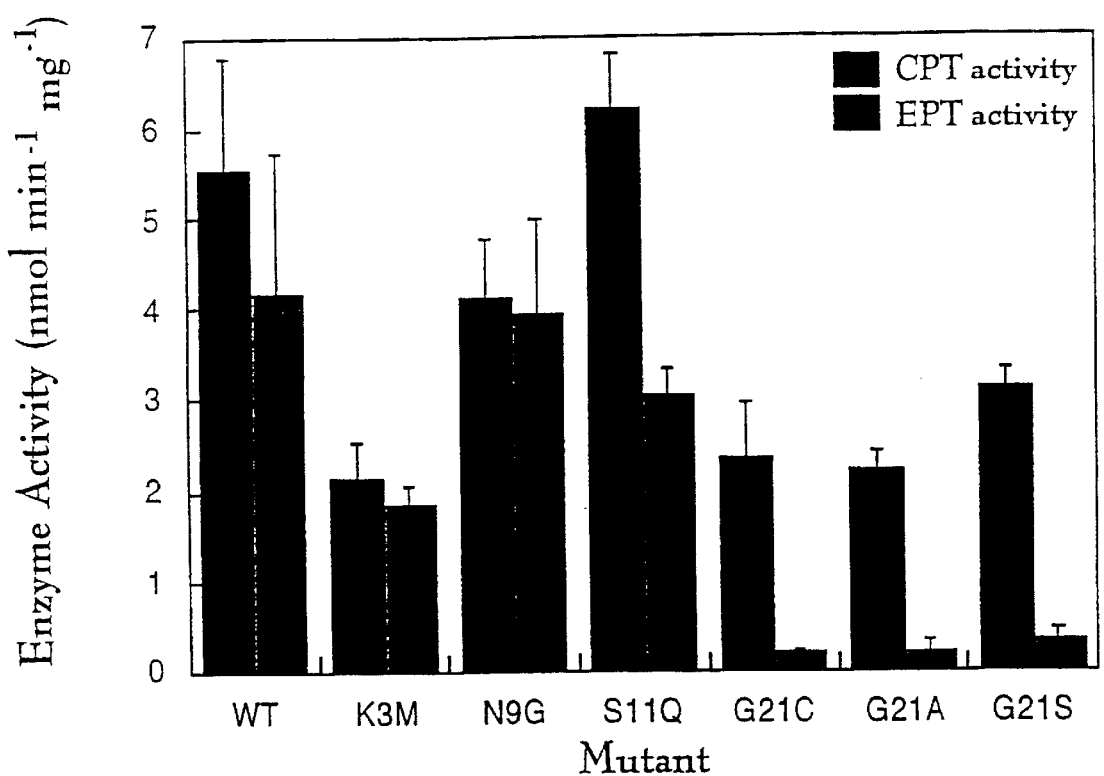
FIG. 7 is a bar graph of in vitro cholinephosphotransferase and ethanolaminephosphotransferase activity in hCEPT1 mutants.
Figure 9:
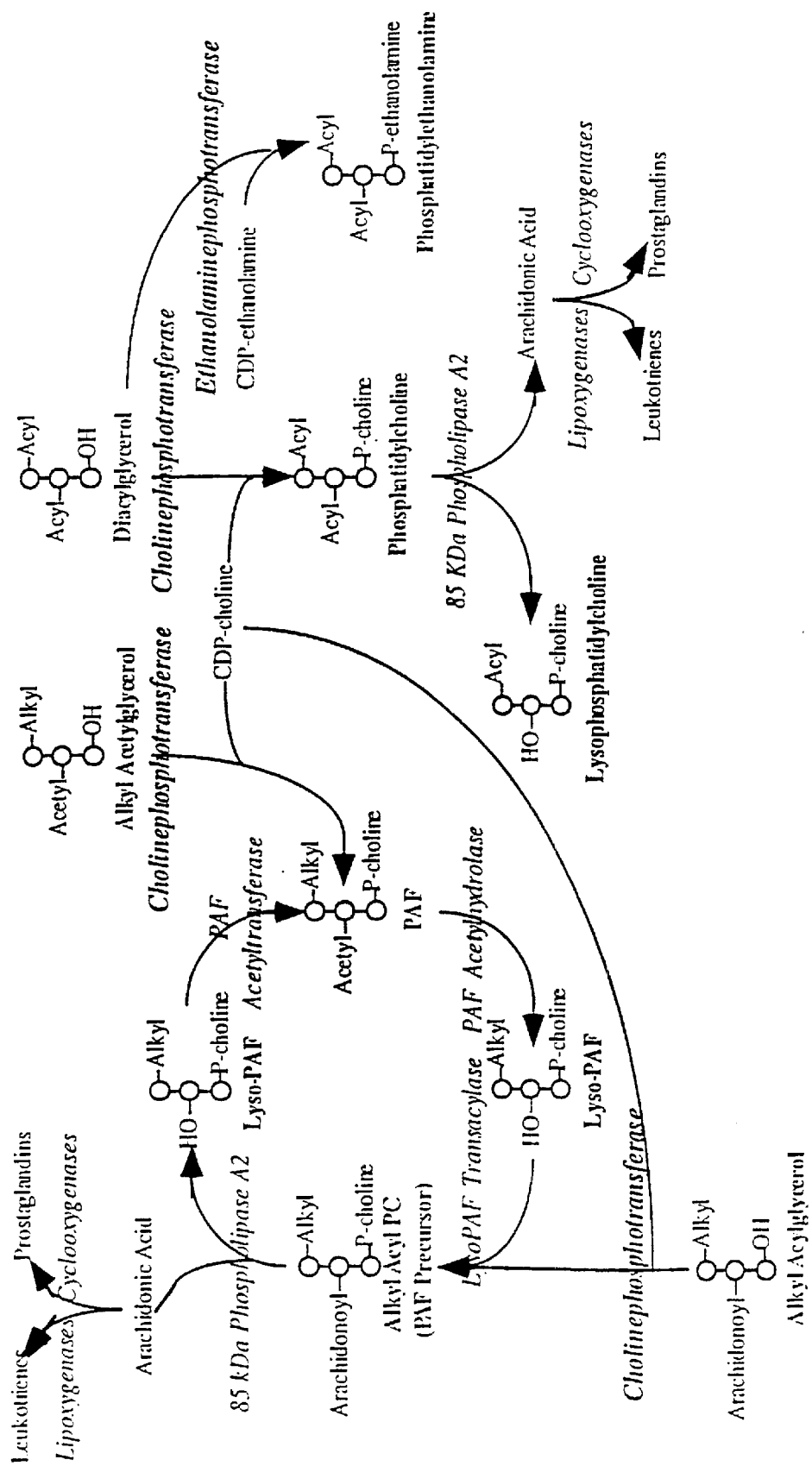
FIG. 9 is a schematic diagram showing the role of choline/ethanolaminaphosphotransferases in lipid formation.

Plasmid pAH9 (Henneberry, A L, and McMaster, C R, 1999, *Biochem. J.* 339: 291–298) contains a T7 epitope tagged version of the hCEPT1 cDNA in the constitutive yeast expression vector pGPD416 (Munberg, D., Muller, R., and Funk, M., 1995, *Gene* 156: 119–122) and was used as the template for all mutagenesis reactions. The T4 DNA polymerase directed MORPH plasmid DNA mutagenesis protocol™ (5 prime-3 prime) was used with the appropriate mutagenic oligonucleotides as directed by the manufacturer. All mutations were confirmed by DNA sequencing. It is of note that as can be seen in FIGS. 7 and 8, mutation of glycine 156 to alanine, serine or cysteine abolished ethanolamine-phosphotransferase activity. Thus, the residue that alters enzyme specificity has been identified, as mutants are no longer able to use CDP-ethanolamine as a substrate.

EXAMPLE VII

ENZYME ASSAYS

Cholinephosphotransferase and ethanolaminephosphotransferase activities were determined using the method of O et al. (O., K-M., Siow, Y. L., and Choy, P. C., 1989, *Biochem. Cell Biol.* 67: 680–686) from microsomal membrane preparations of either HEK293s cells (human kidney cell line) transformed with pcDNA3.1 (mock), pMM6 (hCEPT1) or pCMVsport-hCEPT2 (hCEPT2), or *S. cerevisiae* HJ091 cells (cpt1::LEU2 ept1-, yeast cells devoid of endogenous choline- and ethanolamine-phosphotransferases) transformed with P416GPD (mock), or pAH9 (hCEPT1) and its various mutant derivatives. Diradylglycerols or ceramides were dried under nitrogen gas and resuspended in 0.015% (w/v) Tween 20™ by sonication. Unless otherwise indicated, assay buffer contained 100 mM Tris-HCl (pH 8.0), 20 mM MgCl2, 1 mM EDTA, 1 mM diradylglycerol or ceramide (final Tween 20 concentration of 0.00375%, w/v), and 10 μg of microsomal protein. Components were incubated at room temperature for 5 min followed by the addition of CDP-choline or CDP-ethanolamine (0.2 mM, 2000 dpm/nmol). Assays were incubated at 37° C. for 15 min and activity terminated by the addition of 3 ml CHCl$_3$/CH$_3$OH (2/1, v/v) followed by 1.5 ml 0.9% (w/v) KCl. Tubes were vortexed and phase separation facilitated by centrifugation at 2000 g for 10 min. The aqueous phase was aspirated and the organic phase was washed twice with 1.5 ml 40% (v/v) CH$_3$OH. An aliquot of the organic phase was dried in a scintillation vial and radioactivity was determined. Samples were routinely analyzed by thin layer chromatography on silica gel plates in a solvent system of CHCl$_3$/CH$_3$OH/NH$_4$OH/H$_2$) (70/30/4/2, v/v) to confirm the synthesis of PtdCho, PtdEtn, and PAF and their analogues.

EXAMPLE VIII

PROTEIN AND LIPID DETERMINATION

Protein w as determined by the method of Lowry et al, 1951, *J Biol Chem* 193:265–275 using bovine serum albumin as standard. Diradylglycerols not available commercially were prepared from PtdCho by Bacillus cereus phospholipase C digestion (Boehringer Mannheim) as directed by the manufacturer and yield was estimated using the method of Stern and Shapiro (Stem, I., and Shapiro, B., 1953, *J. Clin. Pathol.* 6: 158–160). Phospholipid phosphorus was determined by the method of Ames and Dubin (Ames, B. N. and Dubin, D. T., 1960, *J. Biol. Chem.* 235: 769–775).

EXAMPLE IX

ANALYSIS OF THE hCEPT1 cDNA PRODUCT

The hCEPT1 coding region predicts a protein of molecular weight 46,550 comprised of 416 amino acid residues of which 48.6% are hydrophobic, as shown in FIG. 2 (SEQ ID NO:2). No signal or sorting sequences were apparent. An expression system devoid of endogenous choline- and ethanolamine-phosphotransferase activities was sought for subsequent enzymological analysis of hCEPT1p. Two systems were explored: (i) prokaryotes are devoid of the Kennedy pathways so hCEPT1 was expressed in *E. coli*; and (ii) hCEPT1 was produced in *S. cerevisiae* strain HJ091 (cpt1::LEU2 ept1-) which contains null mutations at the loci coding for its endogenous choline- (CPT1) and choline/ethanolamine- (EPT1) phosphotransferases (Hjelmstad and Bell, 1990; Hjelmstad et al, 1994). Western blot analysis of T7 epitope tagged hCEPT1p revealed one band of the expected molecular weight of 46,550 was produced in both organisms, as shown in FIG. 3. All of the hCEPT1p detected in *S. cerevisiae* was full length, however, the majority of hCEPT1p produced in *E. coli* had undergone proteolytic degradation. Heterologous expression of hCEPT1 in *S. cerevisiae* HJ091 was utilized for subsequent analyses.

Obvious differences in the efficacy of hCEPT1p to catalyze phosphobase transfer from either CDP-choline or CDP-ethanolamine to various diradylglycerols were apparent (Table 1). Of the diacylglycerols tested, CDP-choline preferred di10:0>>di16:1>di8:0>di18:1 while CDP ethanolamine preferred 16:0/18:1=di18:1=di16:1. High activities were also obtained using alkylacyl 16:0/2:0 or and its diacyl analogue 18:1/2:0, in concert with CDP-choline, resulting in the synthesis of PAF and acyl-PAF.

Kinetic analysis of hCEPT1p (using di18:1 as the diradylglycerol substrate) revealed a Km(app) value of 55 μM for CDP-choline with a Vmax(app) of 40.2 nmol min-1 mg-1, and a Km(app) of 109 μM and Vmax(app) of 12.8 nmol min-1 mg-1 for CDP-ethanolamine. The addition of DTT to the assay mix (0–5 mM) did not affect cholinephosphotransferase activity regardless of the diradylglycerol substrate supplied (data not shown).

EXAMPLE X

TRANSCRIPT LEVELS

A multiple human tissue Northern blot was hybridized with (i) a random primed probe synthesized versus the entire 1.2 kb hCEPT1 coding region, and (ii) a 2.0 kb region of human β-actin. One hCEPT1 transcript of 2.3 kb was observed in all tissue examined and there was no obvious enrichment in any one cell type when normalized to β-actin, as shown in FIG. 4 and as discussed below. Similarly, hCEPT2 transcripts were detected in all cell types tested and were not particularly enriched in any tissue.

EXAMPLE XI

METABOLIC LABELLING

*S. cerevisiae* HJ091 cells (cpt1::LEU2 ept1-) transformed with p416GPD (mock) or pAH9 (hCEPT1) and its various mutant derivatives, were grown to mid-log phase in synthetic dextrose media containing appropriate nutritional supplements to ensure plasmid maintenance (Kaiser, C., Michaelis, S., and Mitchell, A., 1994 in *Methods in Yeast Genetics*, Cold Spring Harbor Press, New York). [$^{14}$C] Choline (10 μM, 1×105 dpm/nmol) was added to the cultures for 1 hr. For [$^{14}$C]ethanolamine experiments, the cells were washed twice in synthetic dextrose media plus required nutritional supplements but without ammonium sulfate, and resuspended in minus ammonium sulfate media before the addition of [$^{14}$C]ethanolamine (6.7 μM, 2.2×105 dpm/nmol) for 1 hr. The reduced nitrogen containing media was required for the efficient uptake of ethanolamine. Subsequent to incubation with radiolabel, cells were concentrated by centrifugation, washed twice with water, and resuspended in 1 ml CHCl$_3$/CH$_3$OH (1/1, v/v). Cells were disrupted for 1 min at 4° C. using a BioSpec Multi Bead Beater containing 0.5 9 of 0.5 mm acid washed glass beads. The beads were washed with 1.5 ml CHCl$_3$/CH$_3$OH (2/1, v/v). To facilitate phase separation 1.5 ml water and 0.5 ml CHCl$_3$ were added. Phospholipids in the organic phase were analyzed by thin layer chromatography on Whatman™ silica gel 60A plates using the solvent system CHCl$_3$ /CH$_3$OH// H$_2$O/ CH$_3$COOH (70/30/4/2, v/v). Aqueous metabolites were concentrated under vacuum, resuspended in H$_2$O and separated by thin layer chromatography on Whatman silica gel 60A plates. Choline containing metabolites were separated in a solvent system consisting of CH$_3$OH/0.6% NaCl/ NH$_4$OH (50/50/5, v/v). Ethanolamine containing metabolites were separated using CH$_3$CH$_2$OH/2% NH$_4$OH (1/2, v/v). Radiolabel was detected using a BIOSCAN™ System 200 imaging scanner to identify and integrate the radioactive bands. This demonstrated the production of the lipid products PtdCho, and PtdEtn in cells expressing active enzyme, and the build up of substrate, CDP-choline or CDP-ethanolamine (and concomitant lack of PtdCho or PtdEtn production) in cells in which inactive enzyme was expressed.

EXAMPLE XII

STRUCTURAL PREDICTIONS

Figure 5:
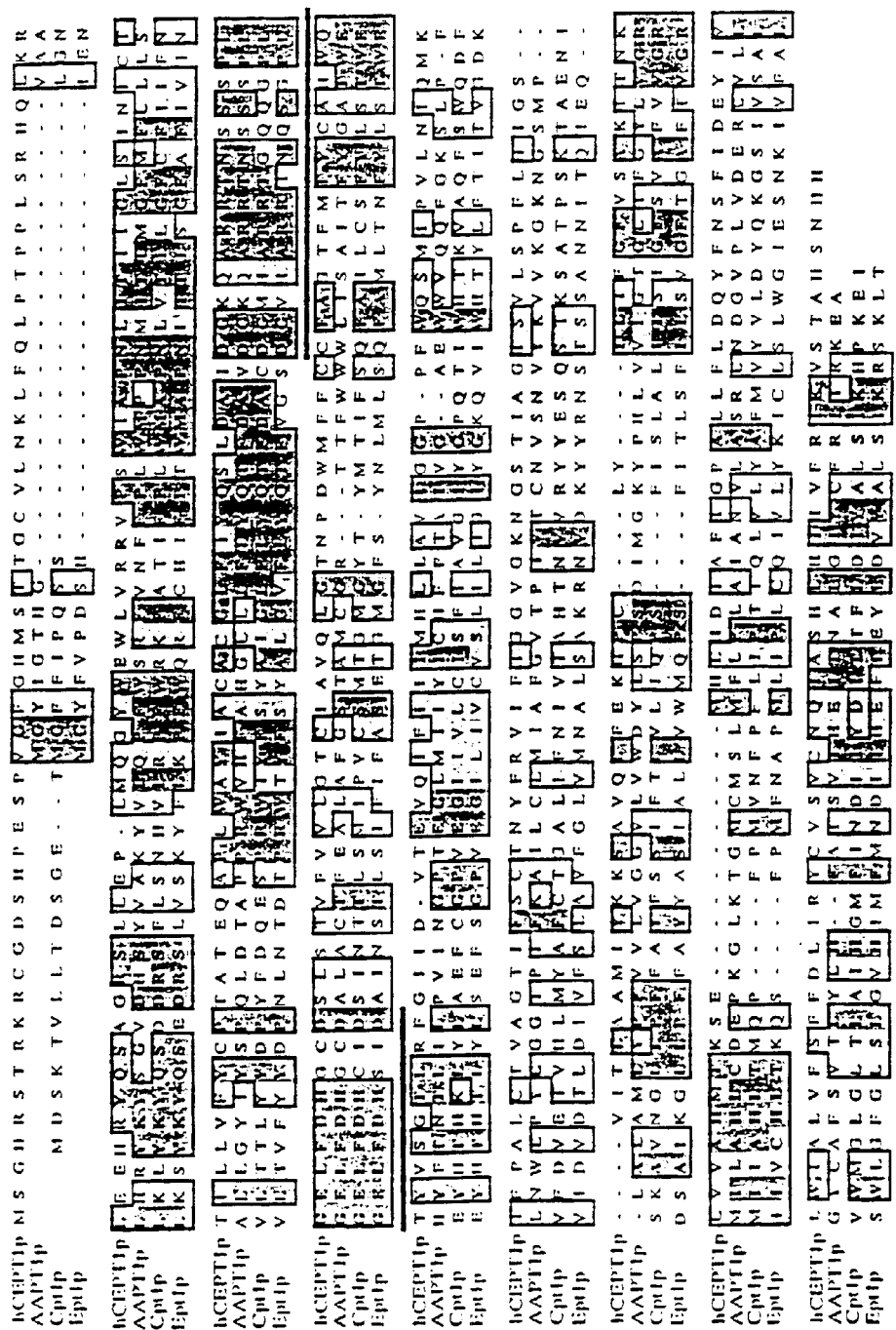
FIG. 5 is an alignment of hCEPT1 protein with known choline-ethanolamine-phosphotranferases.

The CDP-aminoalcohol phosphotransferases Cpt1p and Ept1p from yeast (Hjelmstad and Bell, 1990; Hjelmstad and Bell, 1987), and AAPT1p from soybean (Dewey et al, 1994, *Plant Cell* 6:1495–1507), were aligned with hCEPT1p, as shown in FIG. 5. Specifically, The CLUSTAL-W alignment algorithm set at default parameters was utilized. Underlined residues indicate the positioning of the catalytic CDP-alcohol phosphotransferase motif. Overall identity and similarity levels when compared to hCEPT1p were: 23.1% and 38.2% for yeast Cpt1p; 21.9% and 34.6% for yeast Ept1p, and; 26.9% and 41.8% for plant AAPT1p. Inspection revealed that the CDP-alcohol phosphotransferase motif, DG(x)2AR(x)8G(x)3D(x)3D (SEQ ID NO: 12), spans amino acid residues 136–158 of hCEPT1p and is located in a similar position within the primary sequence of each enzyme, as is evident in FIG. 5.

Membrane spanning domains for each enzyme were estimated using the Tmpred™ algorithm (Hofmann and Stoffel, 1993, *Biol Chem Hoppe-Seyler* 374:166–172) and positioned within each sequence. Specifically, two separate secondary structure algorithms, nnpredict and PHD (Rost and Sander, 1993, *Proc Natl Acad Sci* USA 90:7558–7562; Kneller et al, 1990, *J Mol Biol* 214:171–182), were used to estimate the location of α-helix and β-sheet secondary structures in hCEPT1p. Furthermore, the positioning of amino acid residues of hCEPT1p in a predicted amphipathic helix within the catalytic domain. A strong membrane spanning helix prediction within three out of four of the aligned CDP-aminoalcohol phosphotransferases was the criteria used to position each bilayer spanning region, as shown in FIG. 6.

EXAMPLE XIII

DISCUSSION

The cloned hCEPT1 and hCEPT2 cDNAs code for a choline/ethanolaminephosphotransferase capable of utilizing both CDP-choline and CDP-ethanolamine as phosphobase donors to a broad range of diradylglycerols resulting in the synthesis of PtdCho, PtdEtn, and PAF, as shown in Table1. Kinetic analysis revealed that CDP-choline was the preferred phosphobase donor with a Km(app) of 55 $\mu$M, compared to 109 $\mu$M for CDP-ethanolamine. The highest specific activities were obtained using CDP-choline for phosphoryl transfer to 1O-16:0/2:0 alkylacylglycerol, its structural analogue 18:1/2:0, or di10:0 diacyiglycerol, resulting in the synthesis of PAF, acyl-PAF, and di:10 PtdCho. Previous reports observed several cholinephosphotransferase activities present in eukaryotic cell membranes and DTT sensitivity was used to differentiate an activity capable of synthesizing PAF (DTT-insensitive) from PtdCho (DTT-sensitive) (Snyder, 1997); hCEPT1p cholinephosphotransferase activity was insensitive to DTT regardless of the diradylglycerol substrate supplied.

The hCEPT1 transcript was detected in all cell types tested and was not enriched in any particular tissue. The ubiquitous nature of the hCEPT1 mRNA implies that the enzyme has the capacity to synthesize PtdCho and PtdEtn in vivo, however, its ability to synthesize PAF is difficult to reconcile with its tissue distribution. This is because PAF is normally not present in appreciable amounts but is synthesized in response to extracellular agonists via a specific deacylation/acetylation cycle active in cells of the immune system (Snyder, 1997; Leslie, 1997; Venable et al, 1993). The role of a de novo route for PAF synthesis, and indeed whether the supply of specific diradylglycerols and CDP aminoalcohols affects the ability of hCEPT1p to partition the PtdCho, PtdEtn, and PAF biosynthetic pathways, deserves further characterization. Diacylglycerols have previously been demonstrated to limit the synthesis of both PtdCho (Jamil et al, 1992, *J Biol Chem* 267:1752–1760) and PtdEtn (Tijburg et al, 1989, *Biochem J* 257:645659), consistent with the hypothesis that diradylglycerol levels may affect hCEPT1 p activity and specificity in vivo.

The availability of predicted amino acid sequence data for several CDP-aminoalcohol phosphotransferases facilitated a reexamination of the theorized membrane spanning helices of this class of enzymes from those originally predicted upon the initial cloning of the first cholinephosphotransferase gene, CPT1, from *S. cerevisiae* (Hjelmstad and Bell, 1990; Hoffman and Stoffel, 1993). A rearrangement of the postulated membrane spanning helices is proposed, specifically: amino acid residues corresponding to positions 180–201 within hCEPT1 p were originally predicted to be exist within the solvent but are now envisioned to span the bilayer, and; residues corresponding to 348–368 of hCEPT1p are no longer predicted to reside within the membrane but are now present in the solvent. Of note is an amphipathic helix spanning residues 151–168 of hCEPT1p that is also present within the corresponding region of each CDP-alcohol phosphotransferase (McMaster and Bell, 1997; Williams and McMaster, 1998); the final two aspartate residues of the CDP-alcohol phosphotransferase catalytic motif for each enzyme lie within this amphipathic helix, as shown in FIG. 6. These two aspartate residues are responsible for the nucleophilic attack of the hydroxyl of the hydrophobic diradylglycerol on the phosphoester bond of the water soluble phosphobase substrate (Williams and McMaster, 1998). It is hypothesized that the amphilicity of this helix is required to allow for interface of the two substrates.

A search for regulatory domains within hCEPT1p did not reveal any obvious motifs, however, several interesting regions of similarity were noted. Amino acid residues 18–34 of hCEPT1p align with residues 193–209 of arginosuccinate lyase. A previous study observed cholinephosphotransferase became rate-limiting for PtdCho synthesis in livers of fasted hamsters (Jamil et al, 1992). The inhibitor was purified and identified as arginosuccinate. In addition, residues 252–277 of hCEPT1p align with 89–114 of the PAF receptor (Snyder, 1997; Leslie, 1997; Venable et al, 1993). The *S. cerevisiae* Cpt1p and Ept1p enzymes require activation by their products, PtdCho and PtdCho/PtdEtn, respectively, in amounts indicative of precise phospholipid binding site(s) within the enzyme.

Expression vectors containing host-specific control elements operably linked to the cDNA sequence of either hCEPT1, hCEPT2 or the mutant forms thereof described above can be constructed. As discussed above, these enzymes can be used for transferring phosphocholine or phosphoethanolamine to an acceptor lipid. These may include, but are in no way limited to, diacylglycerols, alkylacylglycerols and alkylalkylglycerols. Thus, the above-described expression vectors may be used to synthesize lipids in vivo, thereby altering the lipid composition of the host organism. This in turn could be used to produce host organisms having a nutritionally more desirable lipid content or having a preferred growth phenotype, as alterations in fatty acid content can also alter membrane fluidity and growth temperatures of organisms.

In other embodiments, purified hCEPT1 and hCEPT2 can be used in vitro to synthesize lipids having a precise fatty acid content for use as a food additive or for other industrial or commercial purposes.

Furthermore, hCEPT1 and hCEPT2 as described above can be used in assay systems for assessing the effect of different compounds on lipid content which can be carried out either in vivo or in vitro. Specifically, hCEPT1 and/or hCEPT2 are provided access to suitable substrates in the presence of at least one compound proposed to have an effect on lipid metabolism. The lipids synthesized by the enzymes can then be analyzed which will in turn indicate what effect the compound is having, that is, whether enzyme activity is being enhanced or repressed or if some substrates or products are preferred. This would allow for the rapid identification of compounds capable of modulating lipid metabolism. Given that the products of hCEPT1 and hCEPT2 include platelet activating factor, which is a mediator of inflammation and phosphatidylcholine, which is a component of lung surfactant, lipoproteins and bile, it is clear that compounds effective in treating a number of disorders, such as chronic and acute pain and inflammation, asthma, allergies, and induction of labour, to name a few, could be identified in this way. Similarly, these compounds could be used to affect other cellular processes, for example, lipoprotein secretion, lung surfactant generation and bile secretion. Furthermore, hCEPT1 and hCEPT2 also produce lipid second messengers, which in turn may be metabolized into leukeotriens and prostaglandins which are in turn mediators of inflammation, it is clear that these compounds could also modulate inflammation. In addition, these compounds could also be used as a means to alter nutritional content and growth phenotypes of other organisms, as discussed above.

Similarly, hCEPT1 and hCEPT2 could be used as gene therapy targets or antisense targets or as enzyme therapy agents for treating any of the disorders listed above. Specifically, antisense RNA directed against either hCEPT1 or hCEPT2 or fragments thereof may be prepared and encapsulated, thereby producing a therapeutic compound for regulating lipid metabolism. Alternatively, purified hCEPT1 and hCEPT2 may be encapsulated and used as a therapeutic compound. In yet other embodiments, DNA sequences encoding hCEPT1 or hCEPT2 may be operably linked to host-specific control sequences for use as a reagent in gene replacement therapy. In these embodiments, the vector would include sequences arranged to direct retention of the vector in the host cell either by positive or negative selection or by directing integration of the DNA into the host genome by means known in the art. In these latter embodiments, the vector may include for example baculovirus sequences, Ti DNA or Autographa Californica nuclear polyhedral virus sequences, or other viral vectors.

Furthermore, reagents such as probes derived from the hCEPT1 and hCEPT2 gene sequences and antibodies directed against the hCEPT1 and hCEPT2 proteins can also be generated. These reagents can in turn be used as diagnostic reagents for diagnosing diseases or genotyping. Alternatively, these reagents can be used to identify related enzymes. That is, nucleotide probes may be used to identify other isoforms of hCEPT1 and/or hCEPT2 for example by library screening or PCR amplification and antibodies directed against the peptides or fragments thereof may be used to identify related enzymes in other organisms for example by library screening.

As discussed above, mutation of glycine 156 of hCEPT1 abolished ethanolaminephosphotransferase activity while cholinephosphotransferase activity remained intact. This residue is also conserved in hCEPT2, indicating that a similar mutant in hCEPT2 would have a similar phenotype. Thus, the residue that alters the enzyme specificity from using both CDP-choline and CDP-ethanolamine to just CDP-choline. This means that the substrate binding/specificity site has been identified. Furthermore, this means that instead of using activity as a measure of enzyme function, this region of either hCEPT1 or hCEPT2 could be expressed and a search for binding/no-binding of substrates, that is, by binding competition experiments to search for inhibitors/drugs could be carried out without actually assaying activity. Specifically, our mutagenesis study has identified the region required for substrate binding. Hence, routine procedures would allow this region of amino acids to be synthesized, or the DNA coding for this region to be expressed as a glutathione-S-transferase fusion protein, His-tagged protein, or other available one step affinity purification systems, for purification of this region. Once purified, radiolabelled substrate (CDP-choline, CDP-ethanolamine, or other CDP-aminoacohol deriviatives) would be predicted to bind this region. ELISA or RIA competition binding experiments (Harlow, E. and Lane, D., 1988 in *Antibodies: A Laboratory Manual*, Cold Spring Harbor Laboratory Press, New York) could be used versus a panel of unknown compounds that would prevent this binding (inhibitors) and thus identify compounds that would alter the activity of hCEPT1 or hCEPT2 enzymes.

Since various modifications can be made in our invention as herein above described, and many apparently widely different embodiments of same made within the spirit and scope of the claims without department from such spirit and scope, it is intended that all matter contained in the accompanying specification shall be interpreted as illustrative only and not in a limiting sense.

TABLE 1

| Diradylglycerol | Enzyme activity (nmol min$^{-1}$ mg$^{-1}$) | |
| --- | --- | --- |
| | CDP-choline | CDP-ethanolamine |
| di8:0 | 54.9 ± 6.4 | 3.1 ± 0.4 |
| di10:0 | 172.5 ± 9.8 | 3.7 ± 0.4 |
| di12:0 | 27.2 ± 6.9 | 2.7 ± 0.3 |
| di14:0 | 6.7 ± 0.2 | 3.7 ± 0.1 |
| di16:0 | 4.3 ± 0.2 | 3.5 ± 0.2 |
| di16:1 | 71.2 ± 8.3 | 13.2 ± 1.1 |
| di18:1 | 40.6 ± 2.7 | 12.2 ± 1.2 |
| 16:0/18:1 | 37.3 ± 2.0 | 14.0 ± 0.8 |
| 18:1/2:0 | 261.5 ± 18.7 | n.d.[1] |
| 1-O-16:0/2:0 | 106.0 ± 5.6 | n.d. |

TABLE 2

| Microsome | CDP-AA | dpm | dpm/ nmol | nmol | nmol/min/ mg | mean |
| --- | --- | --- | --- | --- | --- | --- |
| hCEPT2 | choline | 3172 | 3668 | 0.865 | 10.638 | 10.673 |
| | choline | 3193 | 3668 | 0.871 | 10.708 | |
| | ethanolamine | 551 | 3126 | 0.176 | 2.169 | 2.427 |
| | ethanolamine | 682 | 3126 | 0.218 | 2.685 | |
| 293-S | choline | 465 | 3668 | 0.127 | 1.711 | 1.674 |
| | choline | 445 | 3668 | 0.121 | 1.637 | |
| | ethanolamine | 147 | 3126 | 0.047 | 0.635 | 0.615 |
| | ethanolamine | 138 | 3126 | 0.044 | 0.595 | |
| hCEPT1 | choline | 10306 | 3668 | 2.810 | 13.593 | 13.333 |
| | choline | 9910 | 3668 | 2.702 | 13.072 | |
| | ethanolamine | 2514 | 3126 | 0.804 | 3.892 | 3.910 |
| | ethanolamine | 2538 | 3126 | 0.812 | 3.928 | |

What is claimed is:

1. Purified human choline- and ethanolamineohosphotransferase 1 (hCEPT1) protein of SEQ ID NO:2.

2. An isolated DNA molecule encoding hCEPT1 protein, said DNA deduced from the amino acid sequence according to claim 1.

3. A recombinant expression system, capable, when transformed into a host cell, of expressing the DNA sequence of claim 2 which system comprises control sequences effective in said host cell operably linked to said DNA sequence.

4. A host cell transformed with the expression system according to claim 3.

5. The host cell according to claim 4 wherein the host cell is selected from the group consisting of: a plant cell; a yeast cell; a bacterial cell; and a mammalian cell.

6. Purified hCEPT1 protein according to claim 1 and having a mutation at glycine 156 which has cholinephosphotransferase activity.

7. An isolated DNA molecule encoding mutant hCEPT1 protein, said DNA deduced from the amino acid sequence according to claim 6.

8. A method of synthesizing phosphatidylcholine, or phosphatidylethanolamine factor comprising:
   providing purified hCEPT1 protein of SEQ ID NO:2; hCEPT2 (SEQ ID NO:4); and mutant hCEPT1 protein having;
   providing substrates required for lipid biosynthesis, said substrates consisting of a diraylglycerol and CDP-ethanolamine or CDP-choline;

combining the hCEPT1 protein and the substrates;

incubating the hCEPT1 protein and the substrates under conditions promoting lipid biosynthesis; and harvesting the phosphatidylcholine, or phosphatidylethanolamine.

9. A method of synthesizing phosphatidylcholine comprising:

providing purified hCEPT1 protein having a mutation at glycine 156;

providing substrates required for lipid biosynthesis, said substrates consisting of a diraylglycerols and CDP-choline;

combining the hCEPT1 protein and the substrates;

incubating the hCEPT1 protein and the substrates under conditions promoting lipid biosynthesis; and harvesting the phosphatidylcholine.

* * * * *